(12) United States Patent
Becker et al.

(10) Patent No.: US 11,005,049 B2
(45) Date of Patent: May 11, 2021

(54) METAL COMPLEXES

(71) Applicant: Merck Patent GmbH, Darmstadt (DE)

(72) Inventors: Heinrich Becker, Ober-Ramstadt (DE); Frank Voges, Bad Duerkheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 14/913,086

(22) PCT Filed: Jul. 25, 2014

(86) PCT No.: PCT/EP2014/002035
§ 371 (c)(1),
(2) Date: Feb. 19, 2016

(87) PCT Pub. No.: WO2015/039715
PCT Pub. Date: Mar. 26, 2015

(65) Prior Publication Data
US 2016/0211468 A1 Jul. 21, 2016

(30) Foreign Application Priority Data
Aug. 20, 2013 (DE) ..................... 10 2013 013 876.0

(51) Int. Cl.
| | | |
|---|---|---|
| H01L 51/00 | (2006.01) | |
| C09K 11/06 | (2006.01) | |
| C07F 1/00 | (2006.01) | |
| H01L 51/50 | (2006.01) | |
| C07D 215/26 | (2006.01) | |
| C07F 1/02 | (2006.01) | |
| C09K 11/02 | (2006.01) | |

(52) U.S. Cl.
CPC ........ *H01L 51/0077* (2013.01); *C07D 215/26* (2013.01); *C07F 1/005* (2013.01); *C07F 1/02* (2013.01); *C09K 11/025* (2013.01); *C09K 11/06* (2013.01); *H01L 51/006* (2013.01); *H01L 51/5076* (2013.01); *C09K 2211/1007* (2013.01); *C09K 2211/1011* (2013.01); *C09K 2211/1014* (2013.01); *C09K 2211/181* (2013.01); *H01L 51/0056* (2013.01); *H01L 51/5012* (2013.01); *H01L 51/5072* (2013.01); *Y02E 10/549* (2013.01); *Y02P 70/50* (2015.11)

(58) Field of Classification Search
CPC ............... H01L 51/0077; H01L 51/006; H01L 51/5072; H01L 51/5076; H01L 51/0056; H01L 51/5012; H01L 51/05; H01L 51/42; H01L 51/50; C07F 1/02; C07F 1/005; C07F 5/069; C09K 11/06; C09K 11/025; C09K 2211/181; C09K 2211/1007; C09K 2211/1011; C09K 2211/1014; C09K 2211/186; C07D 215/26; Y02P 70/50; Y02E 10/549
USPC ..................................................... 252/518.1
See application file for complete search history.

(56) References Cited

U.S. PATENT DOCUMENTS

| | | | |
|---|---|---|---|
| 4,255,394 A | 3/1981 | Helgorsky et al. | |
| 4,724,129 A | 2/1988 | Helgorsky et al. | |
| 7,597,926 B2 * | 10/2009 | Kathirgamanathan | ........... C07D 215/30 427/240 |
| 8,679,647 B2 * | 3/2014 | Pflumm | ............ H01L 51/0067 428/690 |
| 8,900,722 B2 * | 12/2014 | Begley | ................ C07D 215/14 428/690 |
| 9,028,562 B2 | 5/2015 | Mignon et al. | |
| 9,409,883 B2 * | 8/2016 | Buesing | ............... C07D 401/10 |
| 9,887,368 B2 * | 2/2018 | Chun | .................. H01L 51/0072 |
| 2007/0073055 A1 | 3/2007 | Organ et al. | |
| 2010/0289009 A1 * | 11/2010 | Ganeshamurugan | ......... H01L 51/0077 257/40 |
| 2011/0006295 A1 * | 1/2011 | Kathirgamanathan | ......... C07D 215/04 257/40 |
| 2011/0095282 A1 | 4/2011 | Pflumm et al. | |
| 2011/0108819 A1 * | 5/2011 | Kathirgamanathan | ......... H01L 51/5072 257/40 |
| 2012/0068170 A1 * | 3/2012 | Pflumm | ............... C07D 413/04 257/40 |
| 2012/0245658 A1 | 9/2012 | Pan et al. | |
| 2012/0292571 A1 * | 11/2012 | Buesing | ............... C07D 401/10 252/301.16 |
| 2014/0048792 A1 | 2/2014 | Chun et al. | |
| 2017/0012221 A1 * | 1/2017 | Buesing | ............... C07D 401/10 |

FOREIGN PATENT DOCUMENTS

| | | |
|---|---|---|
| CA | 2266000 A1 | 9/1999 |
| CN | 1569837 A | 1/2005 |
| CN | 1724541 A | 1/2006 |
| CN | 101041667 A | 9/2007 |
| CN | 101168661 A | 4/2008 |
| CN | 101468966 A | 7/2009 |

(Continued)

OTHER PUBLICATIONS

Kathirgamanathan et al., "Isolation and Characterisation of 2-Tert-butyl-8-hydroxyquinoline as a Crystalline Solid and Its Blue Fluorescent Li Complex", Advances in Materials Science and Engineering, 2014, Article ID 510960, 5 pages.*

(Continued)

*Primary Examiner* — Douglas J McGinty

(74) *Attorney, Agent, or Firm* — Faegre Drinker Biddle & Reath LLP

(57) ABSTRACT

The present invention relates to metal complexes, to compositions and formulations comprising these complexes, and to devices comprising the complexes or compositions.

21 Claims, 1 Drawing Sheet

(56) References Cited

FOREIGN PATENT DOCUMENTS

| | | | |
|---|---|---|---|
| CN | 101597315 A | 12/2009 | |
| CN | 102584697 A | 7/2012 | |
| EP | 1637545 A1 | 3/2006 | |
| EP | 2750214 A2 | 7/2014 | |
| FR | 2974505 A1 | 11/2012 | |
| JP | 53-052289 A | 5/1978 | |
| JP | 54-129000 A | 10/1979 | |
| JP | 07-138266 A | 5/1995 | |
| JP | 09-272865 A | 10/1997 | |
| JP | 11-317291 A | 11/1999 | |
| JP | 2000-021573 A | 1/2000 | |
| JP | 2005-015752 A | 1/2005 | |
| JP | 2007-63489 | 3/2007 | |
| JP | 2007063489 A * | 3/2007 | |
| JP | 2009-272865 A | 11/2009 | |
| JP | 2010-507224 A | 3/2010 | |
| JP | WO 2011157790 A1 * | 12/2011 | ........... C07D 307/91 |
| JP | 2012-513668 A | 6/2012 | |
| JP | 2013-513555 A | 4/2013 | |
| KR | 10-2013-0037186 A | 4/2013 | |
| WO | 2013/051875 A2 | 4/2013 | |

OTHER PUBLICATIONS

STN Reg. No. 1664370-92-6, Mar. 18, 2015.*

Christoph Schmitz et al., "Lithium-Quinolate Compexes as Emitter and Interface Materials in Organic Light-Emitting Diodes", Chem. Mater. 2000, 12, 3012-3019.*

Michael Thompson et al., "Synthesis of the Analytical Ligand 2-tert.-Butyl-8-Hydroxyquinoline", Tallandta, 26, 601-602, 1979.*

Manju Rajeswaran et al., "Steric effects of substituted quinolines on lithium coordination geometry", Polyhedron, 26 (2007) 3653-3660. (Year: 2007).*

Abhishek P. Kulkarni et al., "Electron Transport Materials for Organic Light-Emitting Diodes", Chem. Mater., 2004, 16, 4556-4573. (Year: 2004).*

Barberis et al., "Synthesis and Optical Properties of Aluminum and Zinc Quinolates through Styryl Subsituent in 2-Position", Synthetic Metals, 2006, vol. 156, pp. 865-871.

Rodriguez et al., "Tuning Light Emission Colour of AlQ3 through Oligothiophene Substituents", Organic Optoelectronics and Photonics II, 2006, vol. 6192.

Tuemmler et al., "Open-Chain Polyethers. Influence of Aromatic Donor End Groups on Thermodynamics and Kinetics of Alkali Metal Ion Complex Formation", Journal of the American Chemical Society, 1979, vol. 101, No. 10, pp. 2588-2598.

Database CA XP-002730670 (1986).

Kolobielski, "The Synthesis of Substituted 8-Quinolinols", U.S. Army Coating and Chemical Laboratory, 1966, pp. 275-277.

Thompson et al., "Ultraviolet Photoelectron Spectroscopy and Oxidative Electrochemistry of 8-Hydroxyquinoline and its Derivatives", Analytica Chimica Acta, 1980, vol. 119, pp. 179-185.

Cas Registry No. 1213460-47,9 , Database Registry, [online], 2010, Mar. 23, 2018, Search on Dec. 11, 2016, Retrieved from: STN.

Cas Registry No. 1213602-77,7 , Database Registry, [online], 2010, Mar. 23, 2018, Search on Dec. 11, 2016, Retrieved from: STN.

Cas Registry No. 1225740-66,8 , Database Registry, [online], 2010, May 30, 2018, Search on Dec. 11, 2016, Retrieved from: STN.

Cas Registry No. 1225777-77,4, Database Registry, [online], 2010, May 30, 2018, Search on Dec. 11, 2016, Retrieved from: STN.

Cas Registry No. 1225909-09,0, Database Registry, [online], 2010, May 30, 2018, "Search on Dec. 11, 2016", Retrieved from: STN.

Cheng et al., "Blue and yellow emission from derivates of tris(8-hydroxyquinoline)aluminium light-emitting diodes", Journal of Physics D Applied Physics, vol. 34, No. 17, 2001, pp. 2679-2682.

Harada et al., "Substituent effect of 8 / quinolinolato ligands on photo-induced isomerization for linear nitrosylruthenium(II) complexes-Experimental study", Inorganica Chimica, Acta, vol. 359, 2006, pp. 665-672.

Heiskanen et al., "Absorption and photoluminescence properties of 4-substituted Alq3 derivatives and tris-(4-hydroxypyridinoanthrene)aluminum", Tetrahedron, vol. 65, 2009, pp. 8244-8249.

International Preliminary Report on Patentability received for PCT Patent Application No. PCT/EP2014/002035, dated Mar. 3, 2016, 15 Pages (9 Pages of English Translation and 6 Pages of Original Document).

International Search Report and Written Opinion received for PCT Patent Application No. PCT/EP2014/002035, dated Oct. 28, 2014, 19 pages (9 pages of English Translation and 10 pages of Original Document).

Irving et al., "Sreric Hindrance in Analytical Chemistry. Part V A New 2-Substituted 8-Hydroxyquinolin,e (Oxine)", Journal of the Chemical Society, 1959, pp. 288-290.

Sun et al., "Sodium-Quinolate Complexes as Efficient Electron Injection Materials for Organic Light-Emitting Diode Devices", The Journal of Physical Chemistry C, 115, pp. 2433-2438.

Thompson et al., "Antiamebic Action of 5-Crloro-7-Diethylaminomethyl-8-Quinolinol and of Other Substituted 8-Quinolinols in Vitro and in Experimental Animals", The American journal of tropical medicine and hygiene, 1995, vol. 4, pp. 224-248.

Bankovskis, Latvijas PSR Zinatnu Akademijas Vestis, Kimijas Serija,Synthesis of 2-isopropyl-8-mercaptoquinoline,Sturis,A., vol. 5, 1974, pp. 624-5 (not in English).

Friedrich et al., Chelates of8-quinolinol derivatives. VIII. Acid and complex stability constants of alkyl and alkenyl substituted 8-quinolinols, Chemical Abstracts Service, 1986, 199-205.

Heiskanen et al., 4-Aryl-8-hydroxyquinolines from 4-chloro-8-tosyloxyquinoline using a Suzuki-Miyaura cross-coupling approach, Tetrahedron, vol. 65, No. 2, pp. 518-524.

Manninen et al., "Synthesis and characterization of tris-(5-amino-8-hydroxyquinoline)aluminum complexes and their use as anode buffer layers in inverted organic solar cells", Journal of Materials Chemistry, vol. 22, Issue 43, 2012, pp. 22971-22982.

Nakano et al., "Synthesis of 5-Substituted Quinolin-8-ols", Synthesis, vol. 12, 1997, 1425-1428.

Organ et al., "Biaryls made easy: PEPPSI and the Kumada—Tamao—Corriureaction", Chemistry—A European Journal, vol. 13, No. 1, 2007, pp. 150-157.

Sturis et al., Chemical Papers and Investigation of8-mercaptoquinoline (thiooxine) and its derivatives. 111. Interaction with metal ions and properties of inner complex compounds of 2-propyl-8-mercaptoquinoline, vol. 39, No. 2, 1985, pp. 345-52.

* cited by examiner

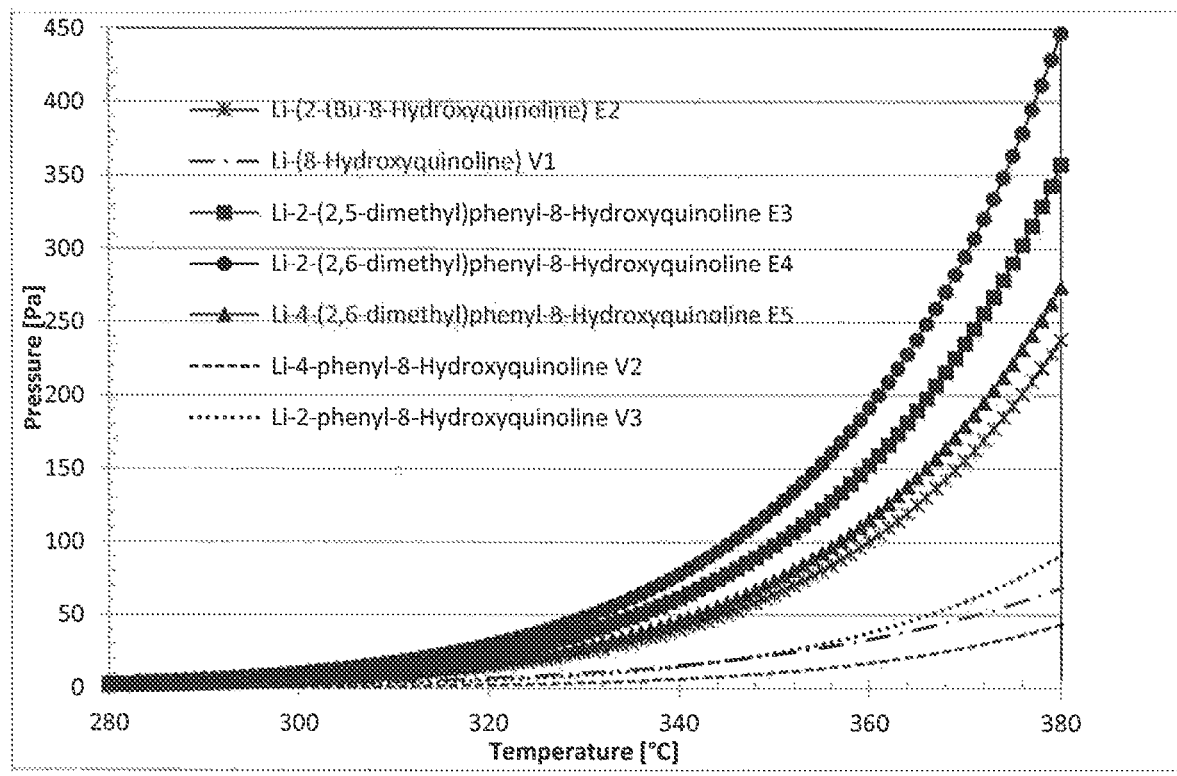

METAL COMPLEXES

RELATED APPLICATIONS

This application is a national stage entry, filed pursuant to 35 U.S.C. § 371, of PCT/EP2014/002035, filed Jul. 25, 2014, which claims the benefit of German Patent Application No. 10 2013 013 876.0, filed Aug. 20, 2013, which is incorporated herein by reference in its entirety.

The present invention relates to metal complexes, to compositions and formulations comprising same, and to devices, in particular electronic devices, comprising the metal complexes and compositions, to the production thereof, and to intermediates of the metal complexes according to the invention.

Electronic devices which comprise organic, organometallic and/or polymeric semiconductors are increasing in importance, where these are employed in many commercial products for cost reasons and owing to their performance. Examples which may be mentioned here are organic-based charge-transport materials (for example triarylamine-based hole transporters) in photocopiers, organic or polymeric light-emitting diodes (OLEDs or PLEDs) in display devices or organic photoreceptors in photocopiers. Organic solar cells (O-SCs), organic field-effect transistors (O-FETs), organic thin-film transistors (O-TFTs), organic integrated circuits (O-ICs), organic optical amplifiers and organic laser diodes (O-lasers) are at an advanced stage of development and may achieve major importance in the future.

Many of these electronic devices have the following general layer structure, irrespective of the particular application, which can be adapted to the particular application:

(1) substrate,
(2) electrode, frequently metallic or inorganic, but also comprising organic or polymeric, conductive materials,
(3) charge-injection layer(s) or interlayer(s), for example for compensation of unevenness of the electrode ("planarisation layer"), frequently comprising a conductive, doped polymer,
(4) organic semiconductors,
(5) possibly further charge-transport, charge-injection or charge-blocking layers,
(6) counterelectrode, materials as mentioned under (2),
(7) encapsulation.

The above arrangement represents the general structure of an organic, electronic device, where various layers can be combined, resulting in the simplest case in an arrangement of two electrodes, between which an organic layer is located. The organic layer in this case fulfils all functions, including the emission of light in the case of OLEDs. A system of this type is described, for example, in WO 90/13148 A1 on the basis of poly-(p-phenylenes).

In order to improve the efficiency and lifetime of electronic devices, metal hydroxyquinoline compounds can be employed in organic layers, in particular in electron-conducting layers, such as, for example, in electron-transport, electron-injection, hole-blocking and emission layers. However, it is disadvantageous that the hydroxyquinoline compounds employed to date have mutagenic effects. Furthermore, the compounds known from the prior art, most of which are applied by vapour deposition, exhibit poor or only moderate processability.

The object of the present invention is therefore the provision of novel compounds and novel devices which overcome the disadvantages known from the prior art. In particular, the compounds and the devices comprising these compounds should be more environmentally friendly or less of a health risk. In particular, an object of the present invention is the provision of compounds having electron-transporting properties with low mutagenicity or a low carcinogenic effect.

Further properties of the device, in particular of the hole-injection materials, hole-transport materials, hole-blocking materials, electron-injection materials, electron-blocking materials and/or emitter materials optionally employed here, should only be impaired to an insignificant extent, or not at all, by the electron-transport materials, such as, for example, efficiency, operating voltage, lifetime, colour coordinates and/or colour purity, i.e. width of the emission band.

A further object can be regarded as being the provision of electronic devices having excellent performance as inexpensively as possible and in constant quality. Furthermore, the novel materials should be better processable and thus better suitable for mass production.

Furthermore, it should be possible to employ or adapt the electronic devices for many purposes. In particular, the performance of the electronic devices should be retained over a broad temperature range.

Surprisingly, it has been found that the compounds, compositions, formulations and devices described in greater detail below achieve these and other objects which are not mentioned explicitly, but which can readily be derived or deduced from the correlations discussed at the outset herein.

The present invention therefore relates to a compound of the general formula (1)

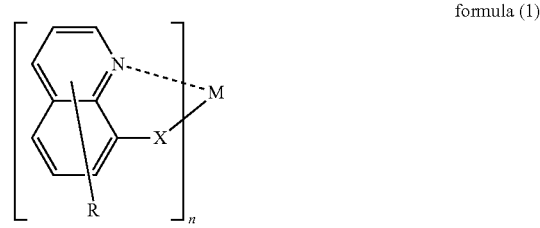

formula (1)

where
M is Al, Zr, Hf, Li, Na, K, Rb, Cs, preferably Al or Li, very preferably Li;
X is S or O, preferably O;
R is a branched or cyclic alkyl or alkoxy group having 3 to 40 C atoms, which may in each case be substituted by one or more radicals $R^a$, where one or more non-adjacent $CH_2$ groups may be replaced by $R^aC=CR^a$, $C≡C$, $Si(R^a)_2$, $Ge(R^a)_2$, $Sn(R^a)_2$, $C=O$, $C=S$, $C=Se$, $C=NR^a$, $P(=O)(R^a)$, SO, $SO_2$, $NR^2$, O, S or $CONR^a$ and where one or more H atoms may be replaced by D, F, Cl, Br, I, CN or $NO_2$, or an aromatic or heteroaromatic ring system, preferably an aromatic ring system, having 5 to 60 aromatic ring atoms, which contains a radical $R^b$ at least in one ortho-position relative to the bonding site to the quinoline ring and may optionally be substituted by one or more radicals $R^a$, where the radical R preferably does not form a ring system together with the quinoline ring;
$R^a$ is on each occurrence, identically or differently, H, D or an alkyl group having 1 to 20 C atoms, an aromatic ring system having 6 to 60 C ring atoms or a heteroaromatic ring system having 1 to 60 C ring atoms, in which, in addition, H atoms may be replaced by D or F; two or more adjacent substituents $R^a$ here may also form a mono- or polycyclic, aliphatic, aromatic or heteroaromatic ring system with one another, where it is preferred for two or more adjacent radicals $R^a$ not to form a ring closure;

$R^b$ is on each occurrence, identically or differently, an alkyl group having 1 to 20 C atoms, an aromatic ring system having 6 to 60 C ring atoms or a heteroaromatic ring system having 1 to 60 C ring atoms, where H atoms may be replaced by D or F; two or more adjacent substituents Rb here may also form a mono- or polycyclic, aliphatic or aromatic ring system with one another, where it is preferred for two or more adjacent radicals $R^b$ not to form a ring closure;

n is 4 for Zr and Hf, 3 for Al and 1 for Li, Na, K, Rb and Cs;

with the proviso that, if R is an aromatic ring system which contains a radical $R^b$ in only one ortho-position to the quinoline ring, the radical $R^b$ has at least 2 C atoms, preferably at least 3 C atoms and very preferably at least 4 C atoms.

The compounds according to the invention have, compared with compounds from the prior art, a lower mutagenic effect in standardised methods. It is assumed that the radicals R according to the invention, which are bulky and project from the plane formed by the quinoline ring system, prevent the mutagenic effect. Other properties of the compounds according to the invention, due to the specific radicals R, may alternatively or additionally be causal for the said advantageous technical effects.

The substituent R may be bonded to the 8-hydroxyquinoline ring or 8-thiooxyquinoline ring (both quinoline ring for short) in any desired position. The numbering on the quinoline ring is specified here as follows:

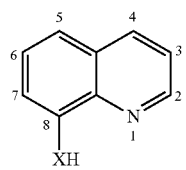

The radical R may accordingly be bonded to the quinoline ring in positions 2, 3, 4, 5, 6 and 7. The radical R is preferably bonded to the quinoline ring in positions 2, 4, 5 and 7, preferably in positions 2 and 4 and very preferably in position 2.

The formulation that two or more radicals may form a ring with one another is, for the purposes of the present application, intended to be taken to mean, inter alia, that the two radicals are linked to one another by a chemical bond. This is illustrated by the following scheme:

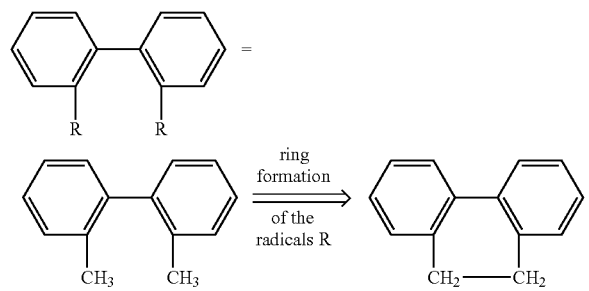

Furthermore, however, the above-mentioned formulation is also intended to be taken to mean that, in the case where one of the two radicals represents hydrogen, the second radical is bonded at the position to which the hydrogen atom was bonded, with formation of a ring. This is intended to be illustrated by the following scheme:

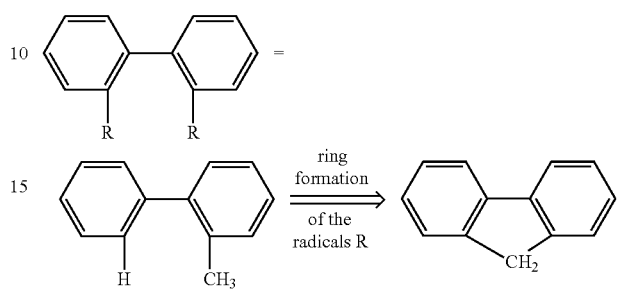

Adjacent radicals in the sense of the present invention are adjacent not only if the atoms to which the radicals are bonded are separated from one another by only one or two chemical bonds, but instead also when the atoms to which the radicals are bonded are separated from one another by more than 2 chemical bonds, so long as the radicals are still in the spatial vicinity of one another.

An aryl group in the sense of this invention contains 6 to 40 C atoms; a heteroaryl group in the sense of this invention contains 2 to 40 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed aryl or heteroaryl group, for example naphthalene, anthracene, phenanthrene, quinoline, isoquinoline, etc.

An aromatic ring system in the sense of this invention contains 6 to 60 C atoms in the ring system. A heteroaromatic ring system in the sense of this invention contains 1 to 60 C atoms and at least one heteroatom in the ring system, with the proviso that the sum of C atoms and heteroatoms is at least 5. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be interrupted by a non-aromatic unit (preferably less than 10% of the atoms other than H), such as, for example, a C, N or O atom or a carbonyl group. Thus, for example, systems such as 9,9'-spirobifluorene, 9,9-diarylfluorene, triarylamine, diaryl ether, stilbene, etc., are also intended to be taken to be aromatic ring systems in the sense of this invention, as are systems in which two or more aryl groups are interrupted, for example, by a linear or cyclic alkyl group or by a silyl group.

Furthermore, systems in which two or more aryl or heteroaryl groups are bonded directly to one another, such as, for example, biphenyl or terphenyl, are likewise intended to be taken to be an aromatic or heteroaromatic ring system.

A cyclic alkyl, alkoxy or thioalkoxy group in the sense of this invention is taken to mean a monocyclic, bicyclic or polycyclic group.

For the purposes of the present invention, a $C_1$- to $C_{40}$-alkyl group, in which, in addition, individual H atoms or CH$_2$ groups may be substituted by the above-mentioned groups, is taken to mean, for example, the radicals methyl, ethyl, n-propyl, i-propyl, cyclopropyl, n-butyl, i-butyl, s-butyl, t-butyl, cyclobutyl, 2-methylbutyl, n-pentyl, s-pentyl, t-pentyl, 2-pentyl, neopentyl, cyclopentyl, n-hexyl, s-hexyl, t-hexyl, 2-hexyl, 3-hexyl, neohexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, dimethyl)octyl, adamantyl, trifluoromethyl, pentafluoroethyl, 2,2,2-trifluoroethyl, 1,1-dimethyl-n-hex-1-yl, 1,1-dimethyl-n-hept-1-yl, 1,1-dimethyl-n-oct-1-yl, 1,1-dimethyl-n-dec-1-yl, 1,1-dimethyl-n-dodec-1-yl, 1,1-dimethyl-n-tetradec-1-yl, 1,1-dimethyl-n-hexadec-1-yl, 1,1-dimethyl-n-octadec-1-yl, 1,1-diethyl-n-hex-1-yl, 1,1-diethyl-n-hept-1-yl, 1,1-diethyl-n-oct-1-yl, 1,1-diethyl-n-dec-1-yl, 1,1-diethyl-n-dodec-1-yl, 1,1-diethyl-n-tetradec-1-yl, 1,1-diethyl-n-hexadec-1-yl, 1,1-diethyl-n-octadec-1-yl, 1-(n-propyl)cyclohex-1-yl, 1-(n-butyl)cyclohex-1-yl, 1-(n-hexyl)cyclohex-1-yl, 1-(n-octyl) cyclohex-1-yl and 1-(n-decyl)cyclohex-1-yl. An alkenyl group is taken to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl. An alkynyl group is taken to mean, for example, ethynyl, propynyl, butynyl, pentynyl, hexynyl, heptynyl or octynyl. A C$_1$- to C$_{40}$-alkoxy group is taken to mean, for example, methoxy, trifluoromethoxy, ethoxy, n-propoxy, i-propoxy, n-butoxy, i-butoxy, s-butoxy, t-butoxy or 2-methylbutoxy.

An aromatic or heteroaromatic ring system having 5-60 aromatic ring atoms, which may also in each case be substituted by the radicals mentioned above and which may be linked to the aromatic or heteroaromatic ring system via any desired positions, is taken to mean, for example, groups derived from benzene, naphthalene, anthracene, benzanthracene, phenanthrene, benzophenanthrene, pyrene, chrysene, perylene, fluoranthene, benzofluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, trans-monobenzoindenofluorene, cis- or trans-dibenzoindenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraaza-perylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

Dopants are generally the materials whose proportion in the system, for example in a layer, is the smaller, and the matrix material or matrix materials are the materials whose proportion in the system is the greater. In individual cases, however, the proportion of an individual matrix material in the system may be smaller than the proportion of an individual dopant. This may be the case if mixed-matrix systems are used.

An n-dopant in the present application is taken to mean an organic or inorganic compound which is capable of releasing electrons (electron donor), i.e. a compound which acts as reducing agent.

The term fluorescent emitter (also called fluorescent dopant) typically encompasses compounds in which the emission of light takes place by a spin-allowed transition from a singlet state.

The term phosphorescent emitter (also called phosphorescent dopant) typically encompasses compounds in which the light emission takes place by a spin-forbidden transition, for example a transition from a triplet state or a state having a higher spin quantum number, for example a quintet state.

Suitable phosphorescent dopants are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent dopants used are preferably compounds which contain copper, molybdenum, tungsten, rhenium, ruthenium, osmium, rhodium, iridium, palladium, platinum, silver, gold or europium, in particular compounds which contain iridium, platinum or copper.

For the purposes of the present application, all luminescent iridium, platinum or copper complexes are regarded as phosphorescent compounds.

Furthermore, R is preferably a branched alkyl group or a cyclic alkyl group containing no heteroatoms.

R particularly preferably contains at least 4 carbon atoms.

Furthermore, R preferably contains 4 to 10 atoms selected from the group consisting of C, N, S and/or O.

In a preferred embodiment of the present invention, the radical R is a branched alkyl group having 4 to 40 C atoms, preferably having 4 to 30 C atoms, very preferably having 4 to 20 C atoms, very particularly preferably having 4 to 10 C atoms and especially preferably having 4 to 6 C atoms, a cyclic alkyl group having 3 to 40 C atoms, preferably having 3 to 30 C atoms, very preferably having 3 to 20 C atoms, very particularly preferably having 3 to 15 C atoms and especially preferably having 6 to 12 C atoms, where the groups may each be substituted by one or more radicals R$^a$ and where one or more H atoms may be replaced by D, F, Cl, Br, I, CN or NO$_2$, or an aromatic ring system having 5 to 60 aromatic ring atoms, which contains a radical Rb at least in one ortho-position relative to the bonding site to the quinoline ring and may optionally be substituted by one or more radicals R$^a$, where preferably none of the radicals R, R$^a$ and R$^b$ forms a ring system with the quinoline ring and where the above-mentioned proviso applies to the ring system substituted in the ortho-position.

In a very preferred embodiment of the present invention, the radical R is a branched alkyl group having 4 to 40 C atoms, preferably having 4 to 30 C atoms, very preferably having 4 to 20 C atoms, very particularly preferably having 4 to 10 C atoms and especially preferably having 4 to 6 C atoms, or a cyclic alkyl group having 3 to 40 C atoms, preferably having 3 to 30 C atoms, very preferably having 3 to 20 C atoms, very particularly preferably having 3 to 15 C atoms and especially preferably having 6 to 12 C atoms, where the groups may each be substituted by one or more radicals $R^a$ and where one or more H atoms may be replaced by D, F, Cl, Br, I, CN or $NO_2$, where preferably none of the radicals R, $R^a$ and $R^b$ forms a ring system with the quinoline ring.

In a further very preferred embodiment of the present invention, the radical R is a cyclic alkyl group having 3 to 40 C atoms, preferably having 3 to 30 C atoms, very preferably having 3 to 20 C atoms, very particularly preferably having 3 to 15 C atoms and especially preferably having 6 to 12 C atoms, where the groups may each be substituted by one or more radicals $R^a$ and where one or more H atoms may be replaced by D, F, Cl, Br, I, CN or $NO_2$, where preferably none of the radicals R, $R^a$ and $R^b$ forms a ring system with the quinoline ring.

In a very particularly preferred embodiment of the present invention, the radical R is a branched alkyl group having 4 to 40 C atoms, preferably having 4 to 30 C atoms, very preferably having 4 to 20 C atoms, very particularly preferably having 4 to 10 C atoms and especially preferably having 4 to 6 C atoms, where the groups may each be substituted by one or more radicals $R^a$ and where one or more H atoms may be replaced by D, F, Cl, Br, I, CN or $NO_2$, where preferably none of the radicals R, $R^a$ and $R^b$ forms a ring system with the quinoline ring.

In an especially preferred embodiment of the present invention, the radical R is a branched alkyl group having 4 to 40 C atoms, preferably having 4 to 30 C atoms, very preferably having 4 to 20 C atoms, very particularly preferably having 4 to 10 C atoms and especially preferably having 4 to 6 C atoms, where the groups may each be substituted by one or more radicals $R^a$ and where one or more H atoms may be replaced by D, F, Cl, Br, I, CN or $NO_2$, where preferably none of the radicals R, $R^a$ and $R^b$ forms a ring system with the quinoline ring.

In an even more preferred embodiment of the present invention, the radical R is a branched alkyl group having 4 to 40 C atoms, preferably having 4 to 30 C atoms, very preferably having 4 to 20 C atoms, very particularly preferably having 4 to 10 C atoms and especially preferably having 4 to 6 C atoms, where the groups are not substituted further and where preferably none of the radicals R, $R^a$ and $R^b$ forms a ring system with the quinoline ring.

In a preferred embodiment of the present invention, $R^a$ in the compound of the formula (1) is not a heteroaromatic ring system.

In a further preferred embodiment of the present invention, $R^b$ in the compound of the formula (1) is not a heteroaromatic ring system.

It is very preferred for the compound of the formula (1) to contain absolutely no further heteroaromatic ring systems besides the quinoline. This has the technical effect that the performance data of electroluminescent devices are better, the processability of the compounds becomes better and the mutagenicity is significantly reduced.

It is therefore preferred for $R^a$ on each occurrence, identically or differently, to be H, D or an alkyl group having 1 to 20 C atoms or an aromatic ring system having 6 to 60 C ring atoms, in which, in addition, H atoms may be replaced by D or F; two or more adjacent substituents $R^a$ here may also form a mono- or polycyclic, aliphatic, aromatic or heteroaromatic ring system with one another, where it is preferred for two or more adjacent radicals $R^a$ not to form a ring closure.

For the same reason, it is therefore also preferred for $R^b$ on each occurrence, identically or differently, to be an alkyl group having 1 to 20 C atoms, an aromatic ring system having 6 to 60 C ring atoms, where H atoms may be replaced by D or F; two or more adjacent substituents $R^b$ here may also form a mono- or polycyclic, aliphatic or aromatic ring system with one another, where it is preferred for two or more adjacent radicals $R^b$ not to form a ring closure.

It is furthermore preferred for $R^a$ on each occurrence, identically or differently, to be H, D or an alkyl group having 1 to 20 C atoms, where two or more adjacent radicals $R^a$ do not form a ring closure.

Particularly preferred radicals R are the groups of the following formulae, where the dashed lines denote the bond to the quinoline of the formula (1):

(R-1)

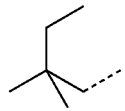
(R-2)

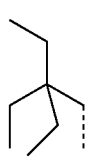
(R-3)

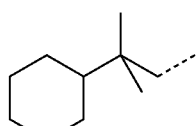
(R-4)

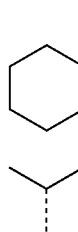
(R-5)

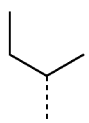
(R-6)

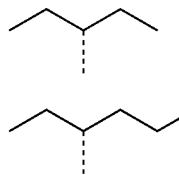
(R-7)

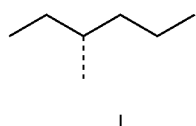
(R-8)

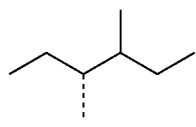
(R-9)

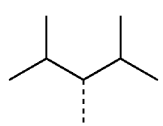
(R-10)

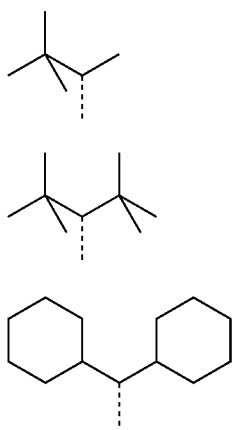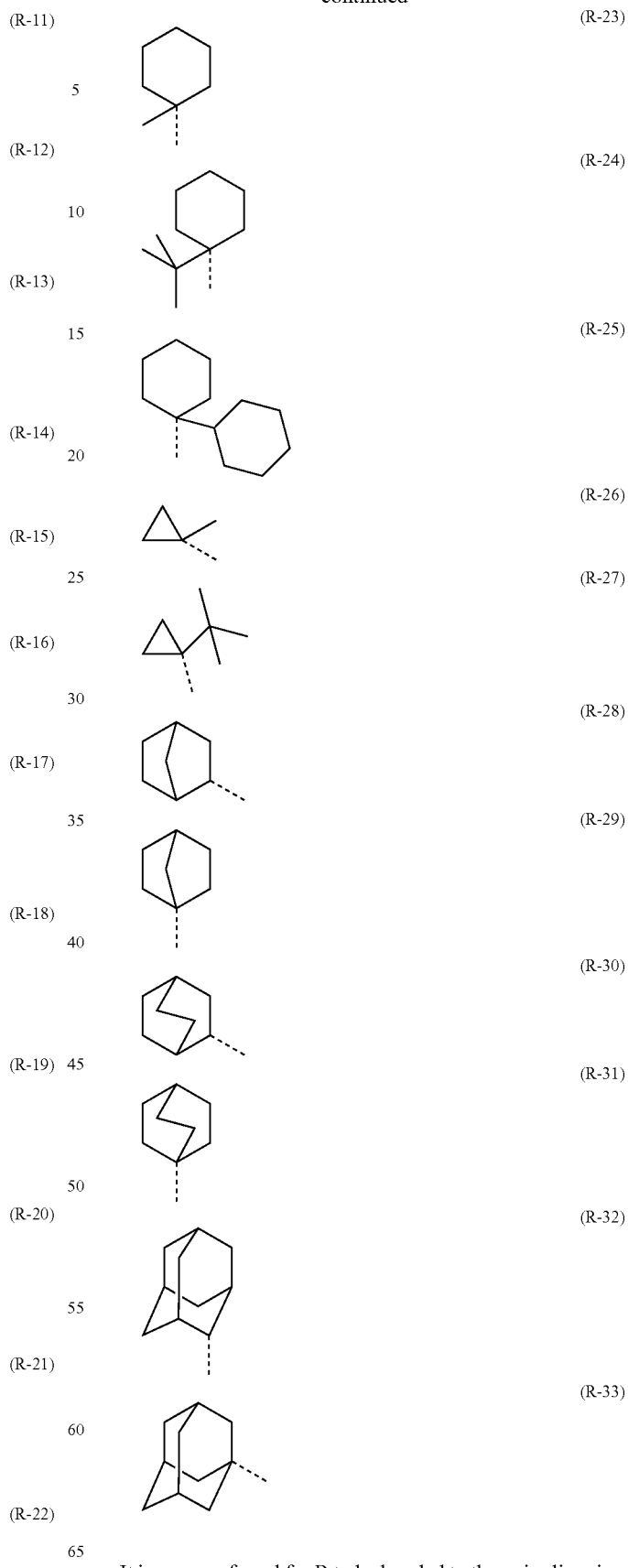
It is very preferred for R to be bonded to the quinoline ring via a quaternary carbon atom.

It is preferred for the purposes of the present invention for the radical $R^a$ to be equal to H.

Particular preference is given for the purposes of the present invention to a compound of the following formula, where the above definitions and the preferred embodiments indicated in the present invention for R, M, X and n also represent preferred embodiments for the compound of the formula (A-1) and where the compound may also be substituted by one or more, identical or different radicals $R^a$, where $R^a$ in the compound of the formula (A-1) is very particularly preferably equal to H:

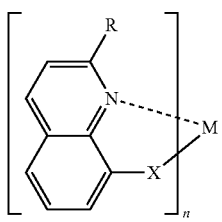

formula (A-1)

Accordingly, very particular preference is also given to a compound of the formula (A-1), where R is a branched alkyl group having 4 to 40 C atoms, preferably having 4 to 30 C atoms, very preferably having 4 to 20 C atoms, very particularly preferably having 4 to 10 C atoms and especially preferably having 4 to 6 C atoms, where the group is not substituted further and where preferably none of the radicals R or $R^a$ forms a ring system with the quinoline ring and where it is even more preferred for M to be equal to Li, X to be equal to O and n to be equal to 1.

The compound of the formula (A-2) is a very preferred compound, where the compound may also be substituted by one or more, identical or different radicals $R^a$, where $R^a$ in the compound of the formula (A-2) is very particularly preferably equal to H. A compound of the formula (A-2) where M is equal to Li, n is equal to 1 and X is equal to O is even more preferred here.

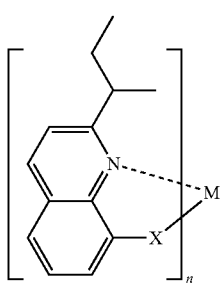

formula (A-2)

The compound of the formula (A-3) is a further very preferred compound, where the compound may also be substituted by one or more, identical or different radicals $R^a$, where $R^a$ in the compound of the formula (A-3) is very particularly preferably equal to H. A compound of the formula (A-3) where M is equal to Li, n is equal to 1 and X is equal to O is even more preferred here.

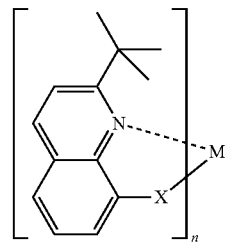

formula (A-3)

The compound of the formula (A-4) is a further very preferred compound, where the compound may also be substituted by one or more, identical or different radicals $R^a$, where $R^a$ in the compound of the formula (A-4) is very particularly preferably equal to H. A compound of the formula (A-4) where M is equal to Li, n is equal to 1 and X is equal to O is even more preferred here.

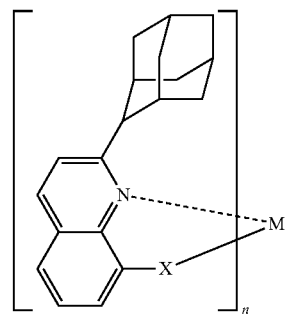

formula (A-4)

The compound of the formula (1) furthermore preferably contains no condensed aromatic or condensed heteroaromatic ring systems having more than 10 ring atoms and very preferably contains absolutely no condensed aromatic or condensed heteroaromatic ring systems.

$R^b$ is furthermore preferably on each occurrence, identically or differently, an alkyl group having 1 to 20 C atoms, where it is preferred for two or more adjacent radicals $R^b$ not to form a ring closure.

Very preferred compounds of the formula (1) are also those of the formulae (B-1) to (B-9), where the compounds may also be substituted by one or more, identical or different radicals $R^a$, where $R^a$ is very particularly preferably equal to H.

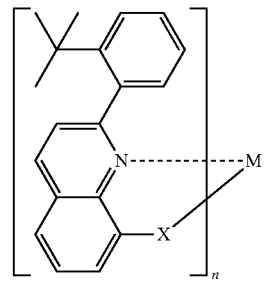

formula (B-1)

-continued
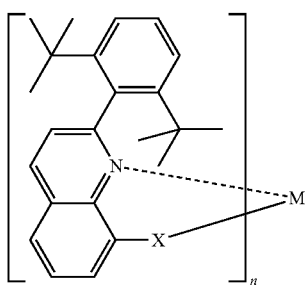
formula (B-2)
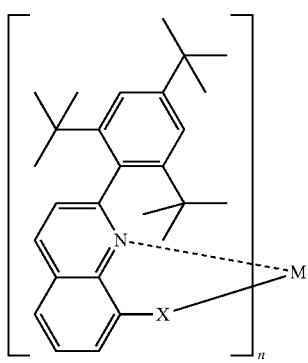
formula (B-2a)
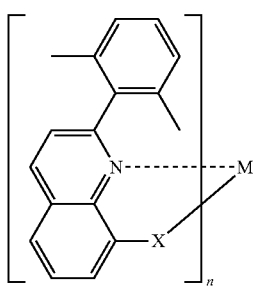
formula (B-3)
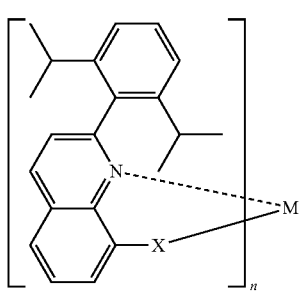
formula (B-4)
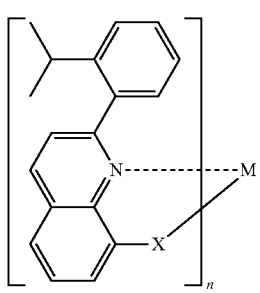
formula (B-5)
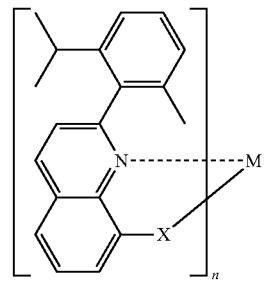
formula (B-6)
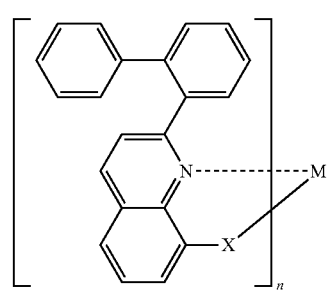
formula (B-7)
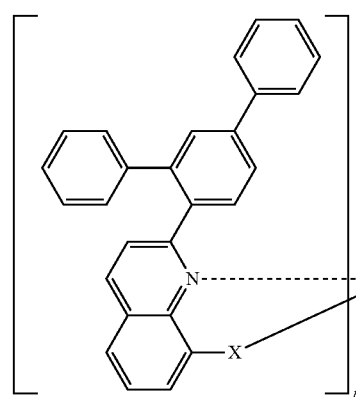
formula (B-8)
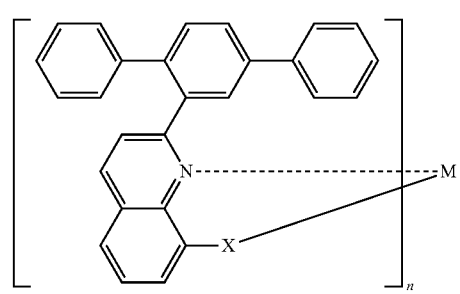
formula (B-9)
A compound of the formulae (B-1) to (B-9) where M is equal to Li, n is equal to 1 and X is equal to O is even more preferred here.
Further examples of compounds according to the invention where M is equal to Li and n is equal to 1 are the compounds of the formulae (C-1) to (C-34) depicted below.

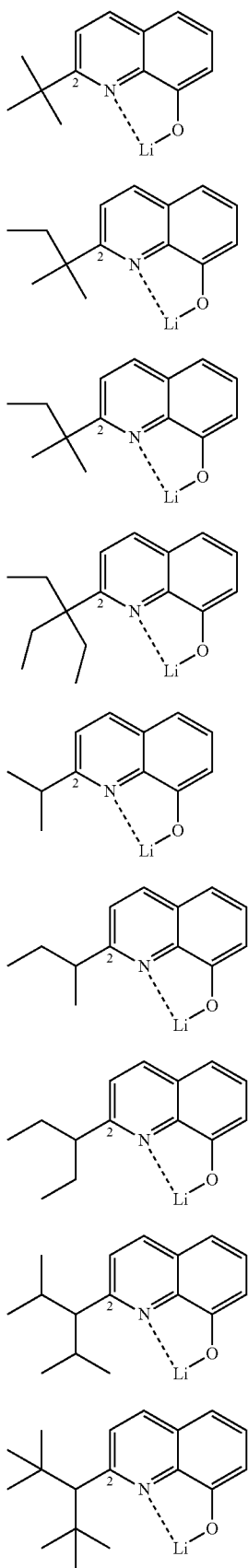

-continued
formula (C-18)
formula (C-19)
formula (C-20)
formula (C-21)
formula (C-22)
formula (C-23)
formula (C-24)
formula (C-25)
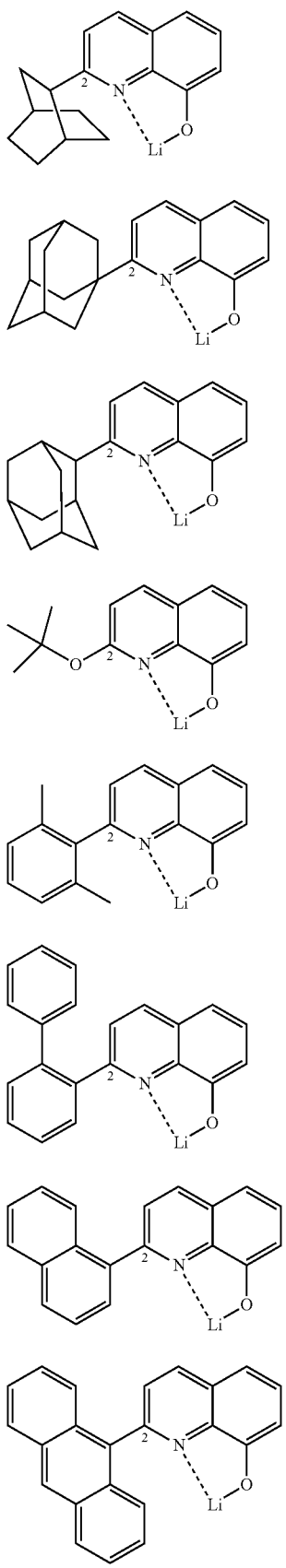
-continued
formula (C-26)
formula (C-27)
formula (C-28)
formula (C-29)
formula (C-30)
formula (C-31)
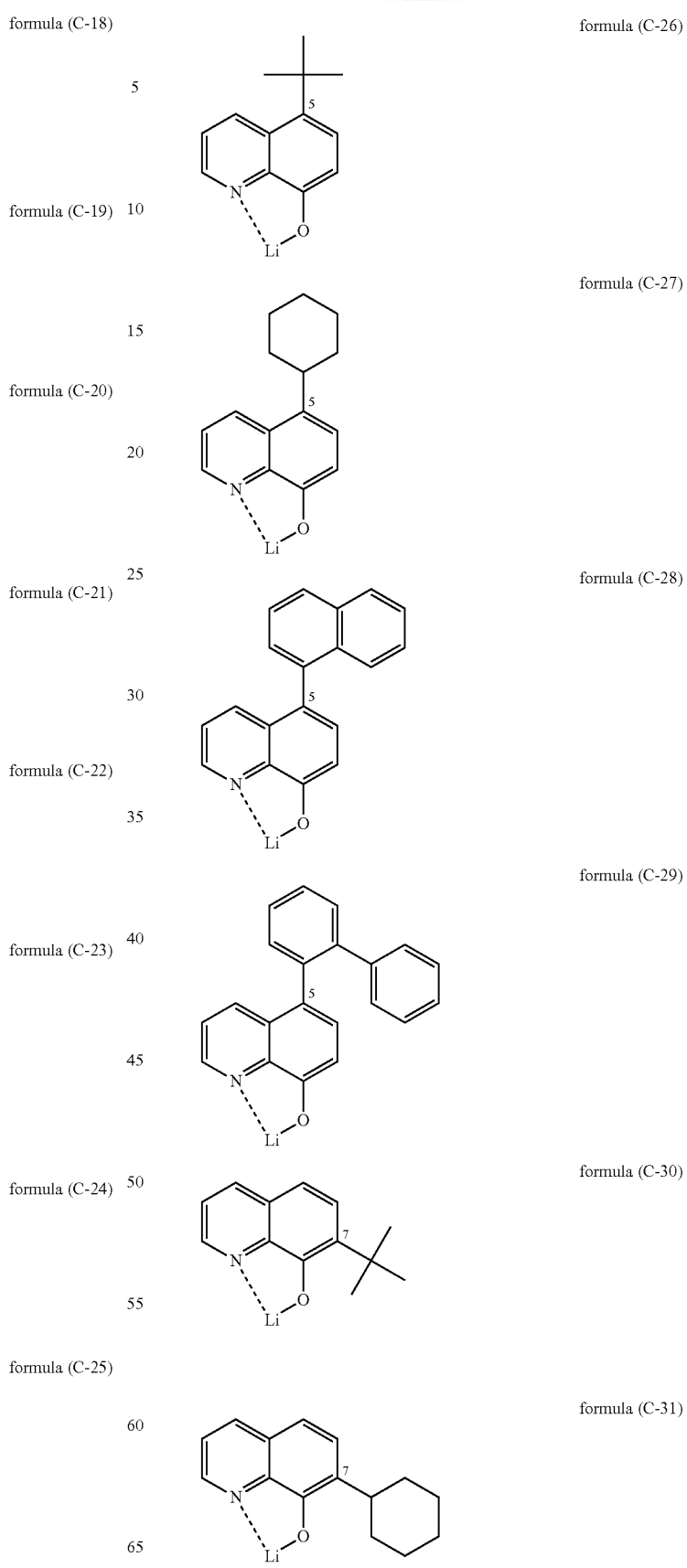

-continued

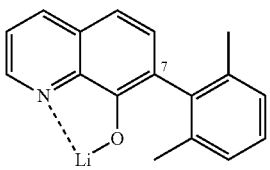

formula (C-32)

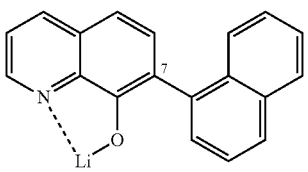

formula (C-33)

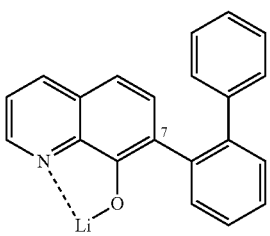

formula (C-34)

Further improvements in efficiency data of devices comprising the compounds can be achieved if the compounds according to the invention are employed in compositions with other materials. The compounds according to the invention are preferably employed in compositions with materials which are typically employed in devices, in particular electronic devices, such as electroluminescent devices.

The present invention therefore also relates to a composition comprising one or more compounds according to the invention and at least one additional functional material selected from the group consisting of fluorescent emitters, phosphorescent emitters, host materials, matrix materials, electron-transport materials, electron-injection materials, hole-conductor materials, hole-injection materials, electron-blocking materials, hole-blocking materials and n-dopants.

The individual materials are well known to the person skilled in the art and he is presented with absolutely no difficulties in selecting suitable compounds from a large available repertoire.

In a further preferred embodiment of the invention, the compounds of the formula (1) are used as a component of mixed-matrix systems. The mixed-matrix systems preferably comprise two or three different matrix materials, particularly preferably two different matrix materials. One of the two materials here is preferably a material having hole-transporting properties and the other material is a material having electron-transporting properties. However, the desired electron-transporting and hole-transporting properties of the mixed-matrix components may also be combined principally or completely in a single mixed-matrix component, where the further mixed-matrix component(s) fulfil(s) other functions. The two different matrix materials may be present here in a ratio of 1:50 to 1:1, preferably 1:20 to 1:1, particularly preferably 1:10 to 1:1 and very particularly preferably 1:4 to 1:1. Mixed-matrix systems are preferably employed in phosphorescent organic electroluminescent devices. Greater details on mixed-matrix systems are given, inter glia, in the application WO 2010/108579.

Particularly suitable matrix materials which can be used in combination with the compounds according to the invention as matrix components of a mixed-matrix system are selected from the preferred matrix materials indicated below for phosphorescent dopants or the preferred matrix materials for fluorescent dopants, depending on what type of dopant is employed in the mixed-matrix system.

The present invention therefore also relates to a composition comprising at least one compound of the formula (1) and at least one further matrix material.

The present invention also relates to a composition comprising at least one compound of the formula (1) and at least one wide band gap material, where a wide band gap material is taken to mean a material in the sense of the disclosure of U.S. Pat. No. 7,294,849. These systems exhibit particularly advantageous performance data in electroluminescent devices.

Systems comprising a plurality of matrix materials (mixed-matrix systems) are employed, in particular, in light-emitting layers of organic electroluminescent devices. The light-emitting layer furthermore also comprises one or more dopants.

In a preferred embodiment of the present invention, the composition comprises at least one additional functional material which is an electron-transport compound besides at least one compound of the formula (1), where the additional functional material is very preferably a non-metallic electron-transport material.

Preferred additional electron-transport materials which are employed in compositions with the compounds according to the invention are pyridines, pyrimidines, pyridazines, pyrazines, oxadiazoles, oxazoles, lactams, quinolines, quinoxalines, anthracenes, benzanthracenes, pyrenes, perylenes, benzimidazoles, triazines, ketones, lactams, phosphine oxides and phenazines and very preferably triazines.

A preferred composition in the sense of the present invention comprises at least one compound of the general formula (1) and an 8-hydroxyquinolinate, which does not fall within the scope of protection of the present invention. In particular, this includes $Hfq_4$, $Zrq_4$, $Alq_3$ and Liq, where q stands for the ligand 8-hydroxyquinolinate. Particular preference is given here to Liq. Ideally, the compound of the formula (1) is present in the composition in a higher concentration than the second quinoline compound. This has the technical advantage that the performance data of electronic devices, in particular of organic electroluminescent devices, are improved further, but the mutagenic compounds can be employed in lower concentrations. Devices comprising these compositions are consequently less of a health risk.

The present invention very preferably relates to compositions comprising at least one compound of the formula (1) and at least one compound of the following formula (2):

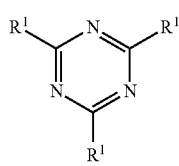

formula (2)

where the following applies to the symbols and indices used:

$R^1$ is on each occurrence, identically or differently, H, D, F, Cl, Br, I, CHO, $N(R^2)_2$, $N(Ar^1)_2$, $B(Ar^1)_2$, $C(=O)Ar^1$, $P(=O)(Ar^1)_2$, $S(=O)Ar^1$, $S(=O)_2Ar^1$, $CR^2=CR^2Ar^1$, CN, $NO_2$, $Si(R^2)_3$, $B(OR^2)_2$, $B(R^2)_2$, B(N(R$^2$)$_2$)$_2$, OSO$_2$R$^2$, a straight-chain alkyl, alkenyl, alkynyl, alkoxy or thioalkoxy group having 1 to 40 C atoms or a branched or cyclic alkyl, alkenyl, alkynyl, alkoxy or thioalkoxy group having 3 to 40 C atoms, each of which may be substituted by one or more radicals R$^2$, where one or more non-adjacent CH$_2$ groups may be replaced by R$^2$C=CR$^2$, C≡C, Si(R$^2$)$_2$, Ge(R$^2$)$_2$, Sn(R$^2$)$_2$, C=O, C=S, C=Se, C=NR$^2$, P(=O)(R$^2$), SO, SO$_2$, NR$^2$, O, S or CONR$^2$ and where one or more H atoms may be replaced by D, F, Cl, Br, I, CN or NO$_2$, or an aromatic or heteroaromatic ring system having 5 to 60 aromatic ring atoms, which may in each case be substituted by one or more radicals R$^2$, or an aryloxy or heteroaryloxy group having 5 to 60 aromatic ring atoms, which may be substituted by one or more radicals R$^2$, or a combination of these systems; two or more adjacent substituents R$^2$ here may also form a mono- or polycyclic, aliphatic or aromatic ring system with one another;

Ar$^1$ is on each occurrence, identically or differently, an aromatic or heteroaromatic ring system having 5 to 30 aromatic ring atoms, which may be substituted by one or more radicals R$^2$; two radicals Ar$^1$ which are bonded to the same nitrogen, phosphorus or boron atom may also be linked to one another here by a single bond or a bridge selected from B(R$^2$), C(R$^2$)$_2$, Si(R$^2$)$_2$, C=O, C=NR$^2$, C=C(R$^2$)$_2$, O, S, S=O, SO$_2$, N(R$^2$), P(R$^2$) and P(=O)R$^2$;

R$^2$ is on each occurrence, identically or differently, H, D or an aliphatic, aromatic and/or heteroaromatic hydrocarbon radical having 1 to 20 C atoms, in which, in addition, H atoms may be replaced by D or F; two or more adjacent substituents R$^2$ here may also form a mono- or polycyclic, aliphatic or aromatic ring system with one another.

The additional electron-transport materials preferably have a glass-transition temperature T$_G$ of greater than 70° C., particularly preferably greater than 90° C., very particularly preferably greater than 110° C., determined in accordance with DIN 51005.

Preference is given here to triazines of the formula (2) in which at least one of the radicals R$^1$, preferably at least two of the radicals R$^1$ and particularly preferably all radicals R$^1$, independently of one another, denote an aromatic or heteroaromatic ring system having 5 to 60 aromatic ring atoms.

It may furthermore be provided that the compound of the formula (2) is a carbazole derivative, preferably an indeno- or indolocarbazole derivative, or a biphenyl derivative, preferably a terphenyl or quaterphenyl derivative.

Furthermore preferred additional electron-transport materials are triazines, which are disclosed in WO 2010/072300 A1. The said triazine compounds can be synthesised, for example, by the processes described in U.S. Pat. Nos. 6,229,012, 6,225,467, WO 05/053055 and DE 102008036982.9.

In a further preferred embodiment of the present invention, the composition comprises at least one additional functional material, which is an n-dopant, besides at least one compound of the formula (1). The n-dopant here may be either an inorganic material or an organic material.

In the case of n-doping, an electron transfer takes place from the HOMO (highest occupied molecular orbital) level of the n-dopant to the LUMO (lowest unoccupied molecular orbital) level of the matrix material, where the electron is generally not strongly localised, but instead counts amongst the charge carriers.

A refinement of the invention proposes that the value of a difference between the HOMO of the n-dopant and the LUMO of the compound according to the invention is preferably less than about 1 eV, further preferably the value of the difference is less than about 0.5 eV.

The compounds according to the invention preferably have an LUMO level of about 1 eV or greater, very preferably 1.5 eV or greater.

Molecular orbitals, in particular also the highest occupied molecular orbital (HOMO) and the lowest unoccupied molecular orbital (LUMO), their energy levels and the energy of the lowest triplet state T$_1$ or the lowest excited singlet state S$_1$ of the materials are determined in the present application with the aid of quantum-chemical calculations. In order to calculate organic substances without metals, firstly a geometry optimisation is carried out using the "Ground State/Semi-empirical/Default Spin/AM1/Charge 0/Spin Singlet" method. An energy calculation is subsequently carried out on the basis of the optimised geometry. The "TD-SCF/DFT/Default Spin/B3PW91" method with the "6-31G(d)" base set is used here (charge 0, spin singlet). For metal-containing compounds, the geometry is optimised via the "Ground State/Hartree-Fock/Default Spin/LanL2MB/Charge 0/Spin Singlet" method. The energy calculation is carried out analogously to the method described above for the organic substances, with the difference that the "LanL2DZ" base set is used for the metal atom and the "6-31G(d)" base set is used for the ligands. The energy calculation gives the HOMO energy level HEh or LUMO energy level LEh in hartree units. The HOMO and LUMO energy levels in electron volts, calibrated with reference to cyclic voltammetry measurements, are determined therefrom as follows:

HOMO(eV)=((*HEh*\*27.212)−0.9899)/1.1206

LUMO(eV)=((*LEh*\*27,212)−2.0041)/1.385

For the purposes of this application, these values are to be regarded as HOMO and LUMO energy levels respectively of the materials.

The lowest triplet state T$_1$ is defined as the energy of the triplet state having the lowest energy which arises from the quantum-chemical calculation described.

The lowest excited singlet state S$_1$ is defined as the energy of the excited singlet state having the lowest energy which arises from the quantum-chemical calculation described.

The method described herein is independent of the software package used and always gives the same results, Examples of frequently used programs for this purpose are "Gaussian09W" (Gaussian Inc.) and Q-Chem 4.1 (Q-Chem, Inc.).

The compounds employed for the n-doping can be employed as precursor, where these precursor compounds liberate n-dopants by activation.

Preferred n-dopants are selected from electron-rich metal complexes; P=N compounds; N-heterocyclic compounds, particularly preferably naphthylenecarbodiimides, pyridines, acridines and phenazines; fluorenes and free-radical compounds.

Particularly preferred electron-rich metal complexes are described, inter alia, in WO 2005/86251 A2, where this specification is incorporated into the present application by way of reference for disclosure purposes. Neutral electron-rich metal complexes are preferred here.

Particularly preferred P=N compounds are disclosed, inter alia, in WO 2012/175535 A1, where this specification is incorporated into the present application by way of reference for disclosure purposes.

A further group of n-dopants is represented by N-heterocyclic compounds. N-heterocyclic compounds are cyclic compounds whose ring structure contains at least one nitrogen atom besides hydrogen and carbon. These compounds may be saturated, partially unsaturated or heteroaromatic.

N-heterocyclic compounds can preferably be employed as precursor, where precursor compounds are distinguished by the fact that their function as n-dopant only commences after activation. Preferred N-heterocyclic compounds which can be employed, in particular, as precursor are described, inter alia, in WO 2009/00237 A1, where this specification is incorporated into the present application by way of reference for disclosure purposes.

A further group of N-heterocyclic compounds which are suitable as n-dopant is represented by naphthylenecarbodiimides. Naphthylenecarbodiimides contain at least one carbodiimide group (N=C=N) and a naphthylene group.

Surprising advantages can be achieved by the naphthylenecarbodiimides described in WO 2012/168358 A1, where this specification is incorporated into the present application by way of reference for disclosure purposes.

The preferred N-heterocyclic compounds which can be employed as n-dopants furthermore include pyridine, acridine and phenazine derivatives. These compounds contain pyridine, acridine and phenazine structural elements and are known in the art. Preferred acridines and phenazines are described, inter alia, in US 2007/0145355 A1, where this specification is incorporated into the present application by way of reference for disclosure purposes.

Surprising advantages can be achieved by the pyridines described in EP 2 452 946 A1 and EP 2 463 927 A1, where these specifications are incorporated into the present application by way of reference for disclosure purposes.

According to a particular embodiment of the present invention, fluorenes can be employed as n-dopants.

Preferred fluorenes are described, inter alia, in WO 2012/031735 A1, where this specification is incorporated into the present application by way of reference for disclosure purposes.

The preferred n-dopants include free-radical compounds which are known in the art. Preferred free-radical compounds contain heterocyclic groups. Particularly preferred free-radical compounds are disclosed, inter alia, in EP 1 837 926 A1 and WO 2007/107306 A1, where these specifications are incorporated into the present application by way of reference for disclosure purposes.

Of the said n-dopants, the electron-rich metal complexes described in WO 2005/86251 A2 are particularly preferred, where the metal complexes of the formula $W_2(hpp)_4$ in which hpp stands for the anion of 1,3,4,6,7,8-hexahydro-2H-pyrimido[1,2-a]pyrimidine are very particularly preferred. Neutral electron-rich metal complexes are particularly preferred here.

The present invention also relates to formulations comprising at least one of the compounds according to the invention or at least one of the compositions according to the invention and at least one solvent.

Formulations of this type are particularly advantageous for processing devices from solution, i.e. from the liquid phase, by means of printing technologies. The processing of the compounds and compositions according to the invention from the liquid phase, for example by spin coating or by printing processes, requires formulations of the compounds and compositions according to the invention. These formulations can be, for example, solutions, dispersions or emulsions. It may be preferred to use mixtures of two or more solvents for this purpose. Suitable and preferred solvents are, for example, toluene, anisole, o-, m- or p-xylene, methyl benzoate, mesitylene, tetralin, veratrol, THF, methyl-THF, THP, chlorobenzene, dioxane, phenoxytoluene, in particular 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetol, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropyl-naphthalene, pentylbenzene, hexylbenzene, heptylbenzene, octylbenzene, 1,1-bis(3,4-dimethylphenyl)ethane or mixtures of these solvents.

The compounds and compositions according to the invention can be used in devices, preferably in electronic devices. The compounds and compositions according to the invention are very preferably used in an organic electroluminescent device, very particularly preferably in an organic light-emitting diode (OLED) or in an organic light-emitting electrochemical cell (OLEC, LEC or also LEEC) and especially preferably in an OLED.

The OLEDs in the present application also include polymeric light-emitting diodes PLEDs.

The present invention also relates to a device comprising at least one of the compounds according to the invention or at least one of the compositions according to the invention.

The devices according to the invention are preferably electronic devices.

Very preferred devices in the sense of the present invention are organic electroluminescent devices, organic integrated circuits, organic field-effect transistors, organic thin-film transistors, organic solar cells, organic optical detectors, organic photoreceptors or organic field-quench devices, where organic electroluminescent devices are very particularly preferred.

Especial preference is given to organic electroluminescent devices selected from the group consisting of organic light-emitting diodes (OLEDs), organic light-emitting transistors, organic light-emitting electrochemical cells (OLECs, LECs or also LEECs) and organic laser diodes, where of these OLEDs and OLECs are even more preferred and where OLEDs are most preferred.

An electronic, in particular electroluminescent, organic device according to the invention comprises at least one organic layer which comprises at least one compound of the formula (1). An organic layer is distinguished by the fact that it comprises at least one organic or organometallic compound. An organic device need not necessarily comprise only layers built up from organic or organometallic materials. Thus, it is also possible for one or more layers to comprise inorganic materials or to be built up entirely from inorganic materials. An organic layer, in particular the organic layer which comprises at least one compound of the formula (1), can preferably comprise at least 30% by vol., very preferably at least 60% by vol., very particularly preferably at least 90% by vol. and especially preferably 100% by vol., of organic or organometallic materials.

The proportion of the compound of the formula (1) in the layer is preferably at least 5% by vol., very preferably at least 15% by vol., very particularly preferably at least 40% by vol., especially preferably at least 60% by vol., even more preferably at least 80% by vol. and most preferably at least 90% by vol. In a very preferred embodiment, the layer consists entirely of a compound of the formula (1).

Compounds of the formula (1) can be employed in the at least one organic layer as the pure substance or as a mixture of two or more compounds of the formula (1). The organic layer can preferably comprise two compounds of the formula (1), which are in the form of a mixture, where the at least two compounds of the formula (1) preferably differ through the position at which R is bonded to the quinoline ring. Particular preference is given here to mixtures which comprise at least one compound of the formula (1) in which the radical R is bonded to the quinoline ring at position 2. Also of particular interest are mixtures comprising at least one compound of the formula (1) in which the radical R is bonded to the quinoline ring at position 5 or 7. The volume ratio of the at least two compounds of the formula (1) in the organic layer can preferably be in the range from 10:1 to 1:10, particularly preferably in the range from 5:1 to 1:5 and especially preferably in the range from 2:1 to 1:2.

The compounds and compositions according to the invention have electron-conducting properties and are preferably located in an electron-conducting layer of the device.

The compounds and compositions according to the invention are preferably located in an electron-transport layer of the device.

The compounds and compositions according to the invention are preferably located in an electron-injection layer of the device.

An electronic device is taken to mean a device which comprises anode, cathode and at least one layer, where this layer comprises at least one organic or organometallic compound. The electronic device according to the invention thus comprises anode, cathode and at least one layer which comprises at least one compound of the formula (1). Preferred electronic devices here are selected from the group consisting of organic electroluminescent devices, preferably organic light-emitting diodes (OLEDs, PLEDs), organic light-emitting transistors (O-LETs), light-emitting electrochemical cells (OLECs) or organic laser diodes, organic integrated circuits (O-ICs), organic field-effect transistors (O-FETs), organic thin-film transistors (O-TFTs), organic solar cells (O-SCs), organic optical detectors, organic photoreceptors, organic field-quench devices (O-FQDs), light-emitting electrochemical cells (LECs) or organic laser diodes (O-lasers).

The cathode preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag, can also be used in addition to the said metals, in which case combinations of the metals, such as, for example, Mg/Ag, Ca/Ag or Ba/Ag, are generally used. It may also be preferred to introduce a thin interlayer of a material having a high dielectric constant between a metallic cathode and the organic semiconductor. Suitable for this purpose are, for example, alkali-metal or alkaline-earth metal fluorides, but also the corresponding oxides or carbonates (for example LiF, $Li_2O$, $BaF_2$, MgO, NaF, CsF, $Cs_2CO_3$, etc.). Likewise suitable for this purpose are organic alkali-metal complexes, for example Liq (lithium quinolinate), where Li hydroxyquinoline of the formula (1) according to the invention is particularly preferred. The layer thickness of this layer is preferably between 0.5 and 5 nm.

The anode preferably comprises materials having a high work function. The anode preferably has a work function greater than 4.5 eV vs. vacuum. Suitable for this purpose are on the one hand metals having a high redox potential, such as, for example, Ag, Pt or Au. On the other hand, metal/metal oxide electrodes (for example $Al/Ni/NiO_x$, $Al/PtO_x$) may also be preferred. For some applications, at least one of the electrodes must be transparent or partially transparent in order to enable either irradiation of the organic material (O-SCs) or the coupling-out of light (OLEDs/PLEDs, O-lasers). Preferred anode materials here are conductive mixed metal oxides. Particular preference is given to indium tin oxide (ITO) or indium zinc oxide (IZO). Preference is furthermore given to conductive, doped organic materials, in particular conductive doped polymers, for example PEDOT, PANI or derivatives of these polymers. It is furthermore preferred for a p-doped hole-transport material to be applied to the anode as hole-injection layer, where metal oxides, for example $MoO_3$ or $WO_3$, or (per)-fluorinated electron-deficient aromatic compounds are suitable as p-dopants. Further suitable p-dopants are HAT-CN (hexacyanohexaaza-triphenylene) or the compound NPD9 from Novaled. A layer of this type simplifies hole injection in materials having a low HOMO, i.e. an HOMO having a large modulus.

According to a preferred embodiment, at least two organic layers may be arranged between the anode and the cathode, where at least two organic layers comprise at least one compound of the formula (1).

In the further layers, it is generally possible to use all materials as are used in accordance with the prior art for the layers, and the person skilled in the art will be able to combine each of these materials with the materials according to the invention in an electronic device without inventive step.

Particular preference is given to organic electroluminescent devices. An organic electroluminescent device comprises cathode, anode and at least one emitting layer (EML). Apart from these layers, it may also comprise further layers, for example in each case one or more hole-injection layers (HIL), hole-transport layers (HTL), hole-blocking layers (HBL), electron-transport layers (ETL), electron-injection layers (EIL), exciton-blocking layers (ExBL), electron-blocking layers (EBL), charge-generation layers and/or organic or inorganic pin junctions. A typical structure of an organic electroluminescent device is: anode/HIL/HTL/EML/ETL/EIL/cathode.

It is possible here for one or more hole-transport layers to be p-doped, for example with metal oxides, such as $MoO_3$ or $WO_3$, or with (per)fluorinated electron-deficient aromatic compounds, and/or for one or more electron-transport layers to be n-doped. Likewise, interlayers which have, for example, an exciton-blocking function and/or control the charge balance in the electroluminescent device may be introduced between two emitting layers. However, it should be pointed out that each of these layers does not necessarily have to be present.

The organic electroluminescent device here may comprise one emitting layer or a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to three-layer systems, where the three layers exhibit blue, green and orange or red emission (for the basic structure see, for example, WO 2005/011013), or systems which have more than three emitting layers. A hybrid system is also possible, where one or more layers fluoresce and one or more other layers phosphoresce.

The organic layer having electron-conducting properties which comprises at least one compound of the formula (1) can preferably be an electron-transport layer or an electron-injection layer.

Furthermore, an organic electroluminescent device comprising anode, cathode, at least one emitting layer and at least one electron-transport layer which is arranged between the emitting layer and the cathode has proven particularly advantageous. The electron-transport layer arranged between the emitting layer and the cathode particularly preferably comprises at least one compound of the formula (1).

The device is correspondingly (depending on the application) structured, provided with contacts and finally hermetically sealed, since the lifetime of such devices is drastically shortened in the presence of water and/or air.

Preference is furthermore given to an electronic device, in particular an organic electroluminescent device, characterised in that one or more layers are applied by means of a sublimation process, in which the materials are applied by vapour deposition in vacuum sublimation units at an initial pressure of usually less than $10^{-5}$ mbar, preferably less than $10^{-6}$ mbar. It is also possible for the initial pressure to be even lower or even higher, for example less than $10^{-7}$ mbar.

Preference is likewise given to an electronic device, in particular an organic electroluminescent device, characterised in that one or more layers are applied by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and thus structured (for example M. S. Arnold et al., Appl. Phys. Lett. 2008, 92, 053301).

Preference is furthermore given to an electronic device, in particular an organic electroluminescent device, characterised in that one or more layers are produced from solution, such as, for example, by spin coating, or by means of any desired printing process, such as, for example, screen printing, flexographic printing, offset printing or nozzle printing, but particularly preferably LITI (light induced thermal imaging, thermal transfer printing) or ink-jet printing. Soluble compounds are necessary for this purpose, which are obtained, for example, by suitable substitution.

The electronic device, in particular the organic electroluminescent device, can also be produced as a hybrid system by applying one or more layers from solution and applying one or more other layers by vapour deposition. Thus, it is, for example, possible to apply an emitting layer comprising at least one emitter and a matrix material from solution and to apply a hole-blocking layer and/or an electron-transport layer thereto by vacuum vapour deposition.

These processes are generally known to the person skilled in the art and can be applied by him without difficulties to electronic devices, in particular organic electroluminescent devices comprising a compound of the formula (1) or the preferred embodiments shown above.

The present invention also relates to the following compound, which represents an intermediate for the preparation of the compound of the formula (1), where the same definitions as apply above for the compound of the formula (1) apply to X and R and to their preferred embodiments.

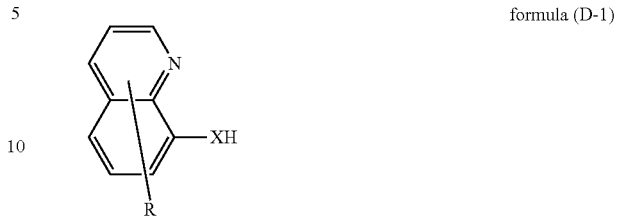

formula (D-1)

The present invention also relates to processes for the preparation of the compounds according to the invention.

The compounds according to the invention can in principle be prepared by various processes. However, the processes described below have proven particularly suitable.

Thus, the compounds of the formula (1) described above can be obtained from 8-hydroxyquinoline via lithium compounds, borono-Minisci reactions and zinc sulfinates.

The preparation of compounds of the formula (1) via lithium compounds starting from 8-hydroxyquinoline in accordance with the general scheme

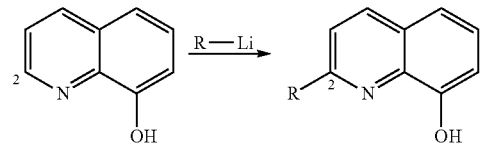

is described, inter alia, in Tetrahedron Asymmetry, 12 (2001), 1345, which is referenced here, where the radical R has the meaning defined above.

Furthermore, the compounds of the formula (1) according to the invention are obtainable via a borono-Minisci reaction in accordance with

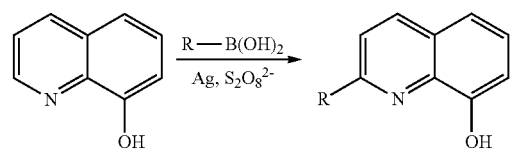

where the radical R has the meaning defined above. Further information regarding preferred embodiments of a borono-Minisci reaction is described in J. Am. Chem. Soc., 2010, 132, 13194.

Zinc sulfinates can likewise be used for the preparation of compounds of the formula (1) according to the invention, in accordance with the scheme

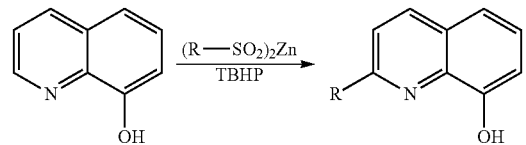

where the radical R has the meaning defined above. Preferred embodiments of this preparation method are described, inter alis, in Nature, 2012, 492, 95.

Furthermore, a bromination of 8-hydroxyquinoline can be carried out, where the brominated 8-hydroxyquinoline is subsequently reacted in a Suzuki or Nigishi reaction. This reaction route is depicted schematically below:

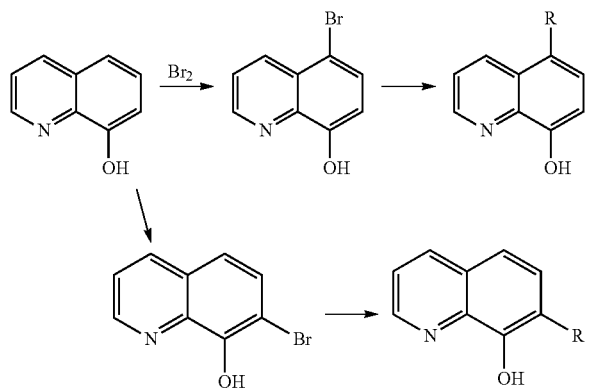

These processes, optionally followed by purification, such as, for example, recrystallisation or sublimation, enable the compounds according to the invention containing structures of the formula (1) and/or formula (2) to be obtained in high purity, preferably greater than 99% (determined by means of $^1$H-NMR and/or HPLC).

The corresponding compounds of the formula (1) where X is equal to S can be prepared analogously.

In a final step, the hydroxyl or thiol compounds are reacted with butyllithium (BuLi) in hexane in order to obtain the metal complex of the formula (1), A solvent which can be used for this purpose is acetonitrile. Details of the process are described in the examples.

Devices comprising the compounds of the formula (1) can be employed in a very versatile manner. Thus, for example, electroluminescent devices comprising one or more compounds of the formula (1) can be employed in displays for televisions, mobile telephones, computers and cameras. However, the devices can also be used in lighting applications. Furthermore, electroluminescent devices, for example in OLEDs or OLECs, comprising at least one compound of the formula (1) can be utilised in medicine or cosmetics for phototherapy. Thus, a multiplicity of diseases (psoriasis, atopic dermatitis, inflammation, acne, skin cancer, etc.) can be treated or skin wrinkling, skin reddening and skin ageing can be prevented or reduced. Furthermore, the light-emitting devices can be used to keep beverages, meals or foods fresh or to sterilise equipment (for example medical equipment).

The present invention therefore relates to an electronic device, preferably an organic electroluminescent device, very preferably an OLED or OLEC and very particularly preferably an OLED, comprising at least one compound of the formula (1) for use for phototherapy in medicine.

The present invention furthermore preferably relates to an electronic device, preferably an organic electroluminescent device, very preferably an OLED or OLEC and very particularly preferably an OLED, comprising at least one compound of the formula (1) for use for the phototherapeutic treatment of skin diseases.

The present invention furthermore very preferably relates to an electronic device, preferably an organic electroluminescent device, very preferably an OLED or OLEC and very particularly preferably an OLED, comprising at least one compound of the formula (1) for use for the phototherapeutic treatment of psoriasis, atopic dermatitis, inflammatory diseases, vitiligo, wound healing and skin cancer.

The present invention furthermore relates to the use of the electronic device, preferably an organic electroluminescent device, very preferably an OLED or OLEC and very particularly preferably an OLED, comprising at least one compound of the formula (1) in cosmetics, preferably for the treatment of acne, ageing skin and of cellulite.

The electronic devices according to the invention, in particular organic electroluminescent devices, are distinguished over the prior art by one or more of the following surprising advantages:

1. Electronic devices, in particular organic electroluminescent devices, comprising a compound of the formula (1) as electron-conducting material have a very good lifetime.
2. Electronic devices, in particular organic electroluminescent devices, comprising a compound of the formula (1) have excellent efficiency.
3. Compounds of the formula (1) in electronic devices, in particular organic electroluminescent devices, enable the formation of optical loss channels to be prevented. These devices are thus distinguished by a high PL efficiency and thus a high EL efficiency of emitters or excellent energy transfer of the matrices to dopants.
4. The use of compounds of the formula (1) in layers of electronic devices, in particular organic electroluminescent devices, results in high mobility of the electron conductor structures.
5. Compounds of the formula (1) are distinguished by excellent thermal stability, where compounds having a molecular weight of less than about 1200 g/mol can be sublimed well.
6. Owing to their advantageous evaporation rate, compounds of the formula (1) can be processed very well and are suitable for the mass production of electronic devices,
7. Compounds of the formula (1) and compositions comprising same exhibit low toxicity and mutagenicity. Furthermore, these compounds and compositions are very environmentally friendly. The low mutagenicity can be demonstrated, in particular, by the AMES test.
8. The compositions according to the invention have improved performance data of electronic devices.

These above-mentioned advantages are not accompanied by an impairment of the other electronic properties.

The above-mentioned preferred embodiments can be combined with one another as desired. In a particularly preferred embodiment of the invention, the above-mentioned preferred embodiments apply simultaneously.

It should be pointed out that variations of the embodiments described in the present invention fall within the scope of this invention. Each feature disclosed in the present invention can, unless explicitly excluded, be replaced by alternative features which serve the same, an equivalent or a similar purpose. Thus, each feature disclosed in the present invention should, unless stated otherwise, be regarded as an example of a generic series or as an equivalent or similar feature.

All features of the present invention can be combined with one another in any way, unless certain features and/or steps are mutually exclusive. This applies, in particular, to preferred features of the present invention, Equally, features of non-essential combinations can be used separately (and not in combination).

It should furthermore be pointed out that many of the features, and in particular those of the preferred embodiments of the present invention, are themselves inventive and should not merely be regarded as part of the embodiments of the present invention. For these features, independent protection may be sought in addition or as an alternative to each invention claimed at present.

The teaching on technical action disclosed with the present invention can be abstracted and combined with other examples.

The person skilled in the art will be able to use the descriptions to produce further electronic devices according to the invention without inventive step and thus carry out the invention throughout the range claimed.

FIG. 1 shows the evaporation curves (p=p(T)) of compounds E2-E5 according to the invention and comparative compounds V1-V3. The curves are at T=380° C. from high pressures to low pressures in the sequence E4, E3, E5, E2, V3, V1 and V2.

EXAMPLES

Example 1

Synthesis of 2-tert-butyl-8-hydroxyquinoline 60 g of 8-hydroxyquinoline (0.41 mol) are dissolved in 200 ml of THF. The solution is cooled to −70° C., 720 ml of 1.7 M (3 eq.) tert-butyllithium are added dropwise. The yellow suspension is stirred at −70° C. for one hour and then slowly warmed to room temperature. 71 g (0.8 mol) of tert-butyl hydroperoxide are then added to this solution, and the mixture is stirred overnight. The solution is extended with 500 ml of toluene and washed once with 1 N HCl and three times with water. The solvent is removed in vacuo, and the residue is chromatographed on silica gel (heptane:ethyl acetate 10:1). The material is recrystallised once from toluene/heptane, giving 41.2 g (0.20 mol, 50%) of 2-tert-butyl-8-hydroxyquinoline as a colourless solid.

Example 2

Synthesis of lithium 2-tert-butyl-8-hydroxyquinoline (E2)

37 g (184 mmol) of 2-tert-butyl-8-hydroxyquinoline from Example 1 are dissolved in 250 ml of acetonitrile. 108 ml of 2.5 M n-BuLi in hexane (270 mmol, 1.5 eq.) are added dropwise at 0° C. After stirring overnight, the solid formed is filtered off, washed with dry acetonitrile and dried, giving 36 g (174 mmol, 95%) of lithium 2-tert-butyl-8-hydroxyquinolinate as a grey solid. The product is sublimed twice in a high vacuum (350° C./1×10$^{-5}$ mbar), giving 26 g (72%) of sublimed product.

Further compounds of the formula (1) according to the invention are prepared analogously.

Example 3

Synthesis of lithium 2-(2,5-dimethylphenyl)-8-hydroxyquinoline (E3)

The synthesis is carried out analogously to the method disclosed in J. Am. Chem. Soc., 2010, 132, 13194.

36 g of 8-hydroxyquinoline (0.25 mol) are dissolved in 125 ml of dichloromethane, and 19 ml (0.25 mol) of trifluoroacetic acid are added. 54 g (0.37 mol) of 2,5-dimethylphenylboronic acid (Frontier Scientific) and 8.5 g (0.05 mol) of silver nitrate are then added. A solution of 100 g (0.38 mol) of potassium peroxodisulfate in 1000 ml of water is added with ice-cooling, and the mixture is warmed to room temperature. The yellow suspension is stirred for 24 hours and extended with 1 l of dichloromethane, the phases are separated, and the organic phase is washed twice with sodium hydrogencarbonate solution. The solvent is removed in vacuo, and the residue is chromatographed on silica gel (heptane:ethyl acetate 10:1). The material is recrystailised once from toluene/acetonitrile, giving 18.2 g (73 mmol, 29%) of 2-(2,5-dimethylphenyl)-8-hydroxyquinoline as a colourless solid.

10 g of the product are converted analogously to Example 2 into 7.1 g of lithium 2-(2,5-dimethylphenyl)-8-hydroxyquinoline, which is sublimed at 330° C.

Example 4

Synthesis of lithium 2-(2,6-dimethylphenyl)-8-hydroxyquinoline (E4)

Analogously to Example 3, 2,6-dimethylphenylboronic acid (Frontier Scientific) is converted into lithium 2-(2,6-dimethylphenyl)-8-hydroxyquinoline and sublimed at 325° C.

Example 5

Synthesis of lithium 4-(2,6-dimethylphenyl)-8-hydroxyquinoline (E5)

10 g (44 mmol) of 4-bromo-8-hydroxyquinoline (Monatshefte für Chemie (1991), 122(11), 935-41) are dissolved in 100 ml of toluene. 100 ml of water, 7.3 g (50 mmol) of 2,6-dimethylphenylboronic acid, 20.2 g (88 mmol) of potassium phosphate hydrate, 200 mg of palladium acetate and 750 mg of 2-dicyclohexylphosphino-2',6'-dimethoxybiphenyl (=S—PHOS) are added. After heating under reflux for 12 hours, the mixture is cooled, the phases are separated and evaporated, and the solid which remains is chromatographed on silica gel (heptane:ethyl acetate 10:1). The material is recrystallised once from toluene/acetonitrile, giving 8.0 g (32 mmol) of 4-(2,6-dimethylphenyl)-8-hydroxyquinoline as a colourless solid. Analogously to Example 2, the material is converted into lithium 4-(2,6-dimethylphenyl)-8-hydroxyquinoline and sublimed at 340° C.

Comparative Example 1

Synthesis of lithium 8-hydroxyquinoline (V1)

Commercial lithium 8-hydroxyquinoline (Green Fine Chemicals) is sublimed twice at 350° C.

Comparative Example 2

Synthesis of lithium 4-(phenyl)-8-hydroxyquinoline (V2)

Analogously to Example 6, lithium 4-(phenyl)-8-hydroxyquinoline is prepared using phenylboronic acid and sublimed at 380° C. Decomposition is observed during the latter.

Comparative Example 3

Synthesis of lithium 2-(phenyl)-8-hydroxyquinoline (V3)

Analogously to Example 3, lithium 2-(phenyl)-8-hydroxyquinoline is prepared using phenylboronic acid and sublimed at 370° C. Decomposition is observed during the latter.

Example 6

Mutagenicity Investigations

Compounds V1 and E2 are subjected to a standardised AMES test (bacteria: *Salmonella typhimurium*; strains TA98, TA100 and TA102). This is referenced by means of DARN (daunomycin), $NaN_3$ (sodium azide), 2-AA (2-aminoanthracene), B(a)p (benzo[a]pyrene) and CUM (cumene hydroperoxide). The test is carried out by the person skilled in the art employing standard methods which are well known in the prior art. The solvent used is DMSO (dimethyl sulfoxide).

The test is carried out both without and also with metabolic activation using an S9 mix.

No mutagenic effect is observed here for the compound from Example 2 and for further compounds according to the invention.

In contrast to the compounds according to the invention, the reference compound, Liq, exhibits significant mutagenicity in all three bacteria strains in the presence of metabolic activation.

The following overview summarises the results of the test for the comparative compound, Liq (V1).

| Metabol. act. | Compound | Conc. [µg/plate] | Revertants/plate (mean ± SD) | | |
|---|---|---|---|---|---|
| | | | TA98 | TA100 | TA102 |
| no | DMSO | | 21 ± 3 | 100 ± 6 | 311 ± 24 |
| no | Liq | 5 | 23 ± 2 | 96 ± 3 | 344 ± 33 |
| no | | 15.8 | 20 ± 4 | 99 ± 2 | 270 ± 30 |
| no | | 50 | 22 ± 1 | 98 ± 4 | 257 ± 59 |
| no | DAUN | 1 | 175 ± 11 | | |
| no | $NaN_3$ | 2 | | 1090 ± 35 | |
| no | CUM | 200 | | | 1481 ± 267 |
| yes | DMSO | | 31 ± 6 | 111 ± 11 | 390 ± 28 |
| yes | Liq | 5 | 31 ± 11 | 146 ± 2 | 559 ± 8 |
| yes | | 15.8 | 40 ± 2 | 261 ± 19 | 697 ± 8 |
| yes | | 50 | 87 ± 1 | 599 ± 115 | 1469 ± 27 |
| yes | | 158 | 100 ± 4 | 788 ± 75 | 911 ± 269 |
| yes | 2-AA | 2 | 201 ± 58 | 384 ± 9 | |
| yes | B(a)p | 10 | | | 2266 ± 18 |

Metabol. act.—Metabolic activation using S9 mix;
Conc.—Concentration;
SD—Standard deviation The following table summarises the results for the compound according to the invention, E2.

| Metabol. act. | Compound | Conc. [µg/plate] | Revertants/plate (mean ± SD) | | |
|---|---|---|---|---|---|
| | | | TA98 | TA100 | TA102 |
| no | DMSO | | 18 ± 3 | 128 ± 21 | 216 ± 18 |
| no | E2 | 5 | 23 ± 11 | 142 ± 25 | 224 ± 6 |
| no | | 15.8 | 29 ± 3 | 133 ± 8 | 217 ± 41 |
| no | | 50 | 18 ± 6 | 104 ± 12 | 237 ± 11 |
| no | | 158 | 20 ± 6$^S$ | 103 ± 1$^S$ | 180 ± 11$^S$ |
| no | | 500 | 14 ± 8$^{SB}$ | 62 ± 17$^{SB}$ | 124 ± 1$^{SB}$ |
| no | | 1580 | 10 ± 4$^{SB}$ | 41 ± 2$^{SBT}$ | 51 ± 18$^{SB}$ |
| no | | 5000 | 17 ± 6$^{SE}$ | 7 ± 3$^{SET}$ | 25 ± 1$^{SE}$ |
| no | DAUN | 1 | 412 ± 80 | | |
| no | $NaN_3$ | 2 | | 743 ± 52 | |
| no | CUM | 200 | | | 912 ± 59 |
| yes | DMSO | | 30 ± 3 | 155 ± 11 | 252 ± 15 |
| yes | E2 | 5 | 24 ± 6 | 199 ± 4 | 302 ± 18 |
| yes | | 15.8 | 30 ± 2 | 132 ± 11 | 255 ± 8 |
| yes | | 50 | 33 ± 4 | 143 ± 8 | 245 ± 22 |
| yes | | 158 | 30 ± 3$^S$ | 147 ± 8$^S$ | 142 ± 22$^S$ |
| yes | | 500 | 25 ± 7$^{SB}$ | 108 ± 1$^{SB}$ | 89 ± 11$^{SB}$ |
| yes | | 1580 | 18 ± 5$^{SB}$ | 57 ± 16$^{SBT}$ | 62 ± 3$^{SB}$ |
| yes | | 5000 | 13 ± 1$^{SE}$ | 4 ± 3$^{SET}$ | 37 ± 1$^{SE}$ |
| yes | 2-AA | 2 | 1376 ± 44 | 1365 ± 18 | |
| yes | B(a)p | 10 | | | 2751 ± 280 |

$^S$Plate as suspension;
$^B$Failed at the beginning of the experiment;
$^E$Failed by the end of the experiment;
$^T$Toxicity = reduced bacterial background lawn

Example 7

Characterisation of the Vapour-Deposition Behaviour

The vapour-deposition behaviour is investigated by means of the "effusion method" (J- Pestic. Sci. 1982, 13, 161-168). The results are summarised in FIG. 1. Compounds E2-E5 according to the invention have significantly better evaporation than comparative compounds V1-V3.

Example 8

Production and Characterisation of the OLEDs

OLEDs according to the invention and OLEDs in accordance with the prior art are produced by a general process in accordance with WO 2004/058911, which is adapted to the circumstances described here (layer-thickness variation, materials).

The data of various OLEDs are presented in the following inventive example E1 and in the reference example V1. The substrates used are glass plates coated with structured ITO (indium tin oxide) in a thickness of 50 nm. The OLEDs have in principle the following layer structure: substrate/p-doped hole-transport layer A' (HIL1)/hole-transport layer A (HTL)/hole-transport layer C (EBL)/emission layer (EML)/electron-transport layer (ETL)/electron-injection layer (EIL) and finally a cathode. The cathode is formed by an aluminium layer with a thickness of 100 nm. The materials required for the production of the OLEDs are shown in Table 1, the structure of the various electronic devices produced is shown in Table 2.

All materials are applied by thermal vapour deposition in a vacuum chamber. The emission layer here always consists of at least one matrix material (host material) and an emitting dopant (emitter), which is admixed with the matrix material or matrix materials in a certain proportion by volume by co-evaporation. An expression such as H1:SEB (95%:5%) here means that material H1 is present in the layer in a proportion by volume of 95% and SEB is present in the layer in a proportion of 5%. Analogously, the electron-transport layer or the hole-injection layers may also consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current/voltage/luminous density characteristic lines (IUL characteristic lines) assuming Lambert emission characteristics, and the lifetime are determined. The electroluminescence spectra are determined at a luminous density of 1000 cd/m$^2$, and the CIE 1931 x and y colour coordinates are calculated therefrom. The term EQE @ 10 mA/cm$^2$ denotes the external quantum efficiency at a current density of 10 mA/cm$^2$. LT80 @ 60 mA/cm$^2$ is the lifetime by which the OLED has dropped to 80% of the initial intensity at a constant current of 60 mA/cm$^2$.

TABLE 1

Structures of the materials used

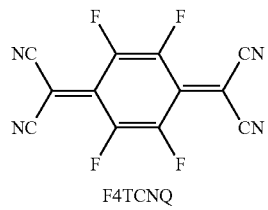 [SMILES: N#CC(C#N)=c1c(F)c(F)c(=C(C#N)C#N)c(F)c1F]

F4TCNQ

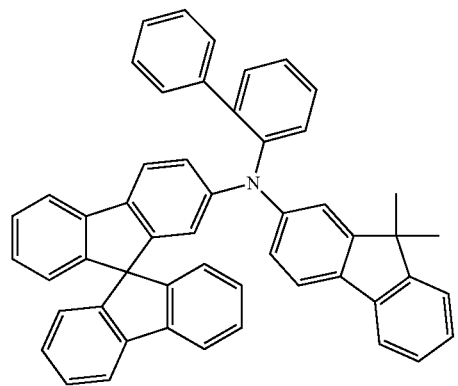

HIM

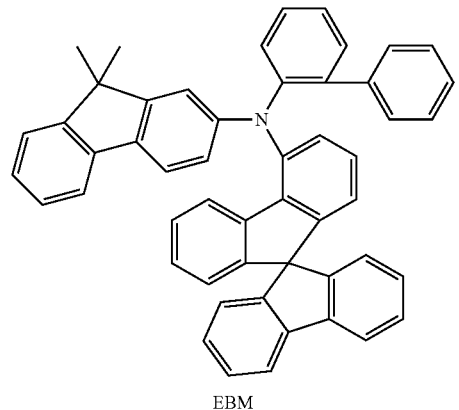 [SMILES: CC1(C)c2ccccc2-c2ccc(N(c3ccccc3-c3ccccc3)c3cccc4c3-c3ccccc3C43c4ccccc4-c4ccccc43)cc21]

EBM

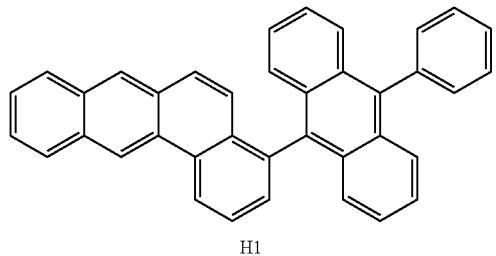

H1

TABLE 1-continued

Structures of the materials used

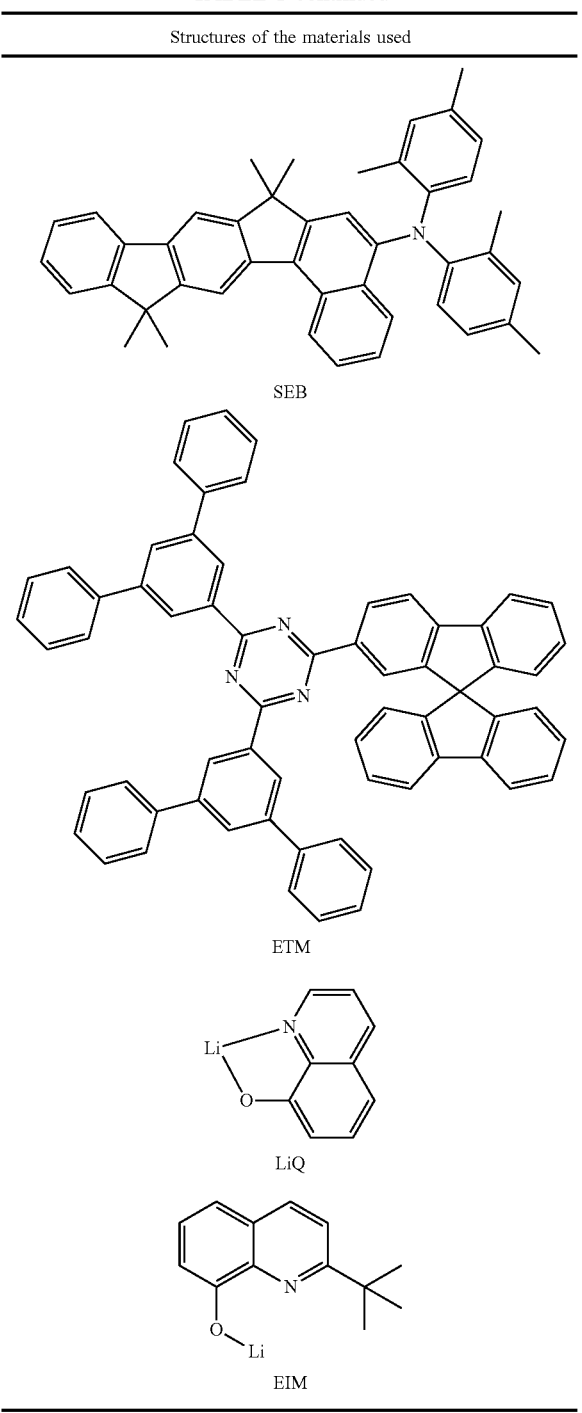

SEB

ETM

LiQ

EIM

Sample E2 according to the invention requires approximately the same voltage of 3.7 V at 10 mA/cm² as reference sample V1 with 3.8 V. Sample E1 according to the invention requires a slightly higher voltage of 4.3 V than the reference sample. Sample E2 also has a comparable efficiency of 8.9% EQE at 10 mA as the reference sample with 8.9% EQE, while sample E1 has a somewhat lower efficiency of 8.2% EQE. Sample E1 has a somewhat better lifetime LT80 of 215 h at 60 mA/cm² than reference sample V1. Sample E2 has a somewhat shorter lifetime of 125 h. Even though all characteristic data for the LiQ samples are not identical, it can be shown that very good lifetimes and high efficiencies can be achieved with the novel LiQ derivative.

It should be noted here that the OLEDs used here do not represent optimised devices, and it is possible for the person skilled in the art, without inventive step, to increase the efficiency of the OLEDs by suitable measures familiar to him. Such an increase in the efficiency can be observed, for example, if compositions according to the invention are employed instead of the individual compounds in the corresponding layers.

The invention claimed is:
1. A composition comprising a compound of formula (1):

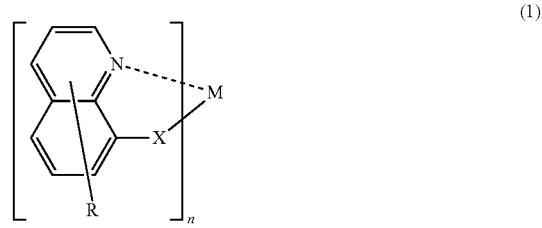

wherein
M is Li;
X is O;
R is a group of formulae (R-1) through (R-33), wherein the dashed line denotes the bond to the quinoline ring of the compound of formula (1):

TABLE 2

| Ex. | HIL1 Thickness/nm | HTL Thickness/nm | EBL Thickness/nm | EML Thickness/nm | ETL Thickness/nm | EIL Thickness/nm |
|---|---|---|---|---|---|---|
| V1 | HIM1:F4TCNQ(5%) 10 nm | HIM1 190 nm | EBM 10 nm | H1:SEB(5%) 20 nm | ETM(50%):LiQ(50%) 30 nm | LiQ 1 nm |
| E1 | HIM1:F4TCNQ(5%) 10 nm | HIM1 190 nm | EBM 10 nm | H1:SEB(5%) 20 nm | ETM(50%):EIM(50%) 30 nm | EIM 2 nm |
| E2 | HIM1:F4TCNQ(5%) 10 nm | HIM1 190 nm | EBM 10 nm | H1:SEB(5%) 20 nm | ETM 30 nm | EIM 3 nm |

-continued
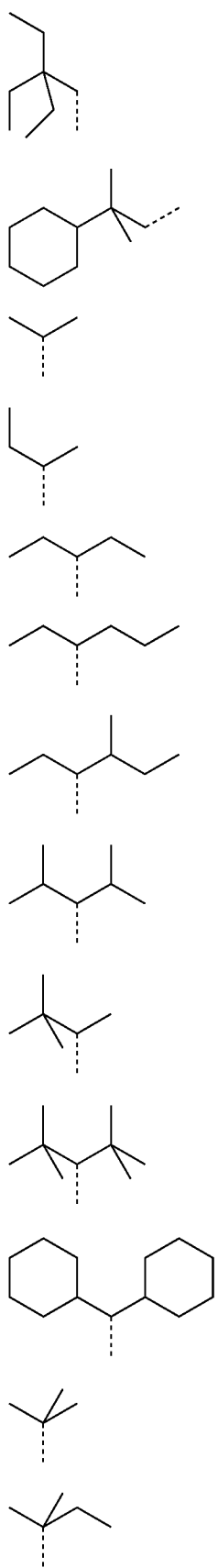
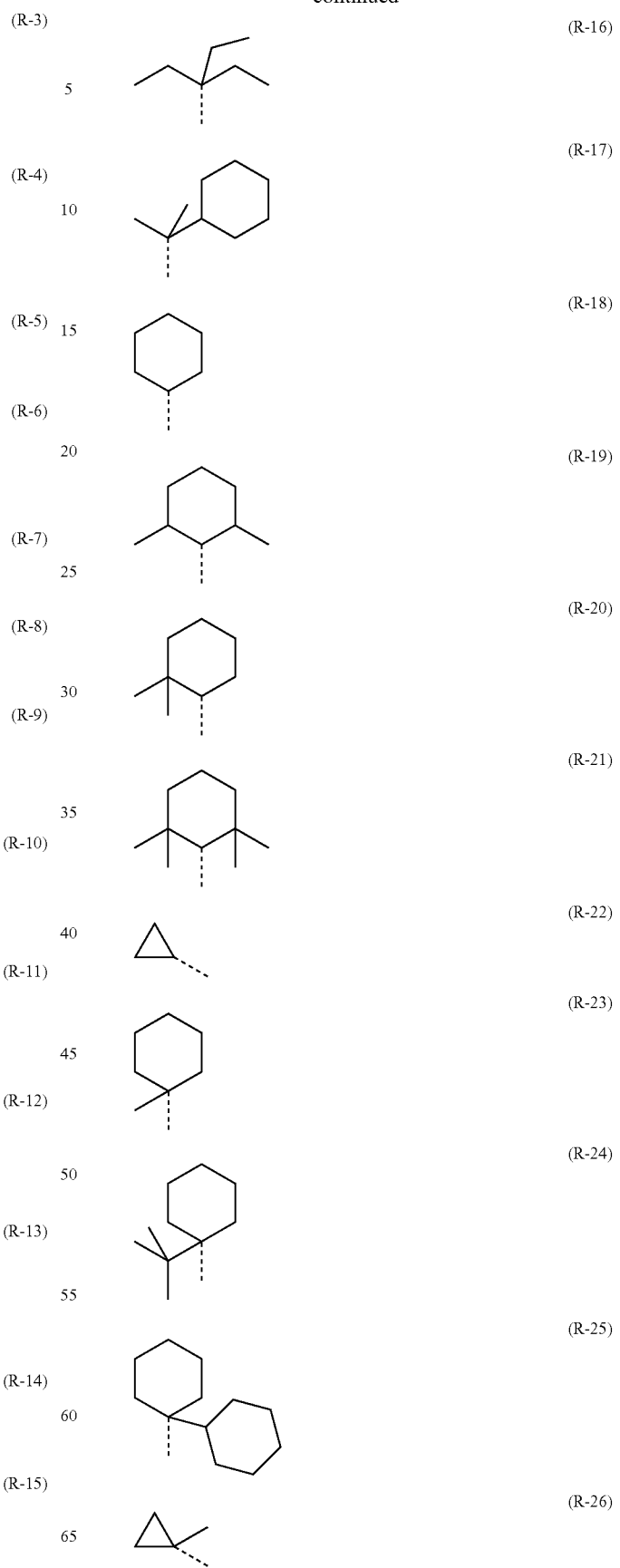

(R-27) 

(R-28) 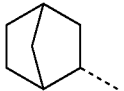

(R-29) 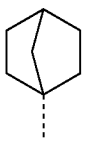

(R-30) 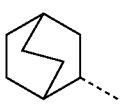

(R-31) 

(R-32) 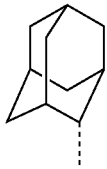

(R-33) 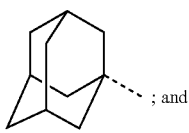 ; and n is 1;

wherein R is bonded to the quinoline ring at position 2; and an electron-transport material comprising at least one triazine.

2. The composition of claim 1, wherein the compound is a compound of formulae (A-2) through (A-4):

(A-2) 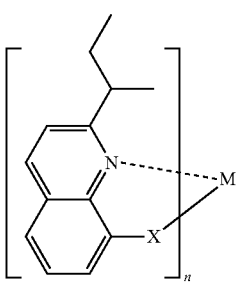

(A-3) 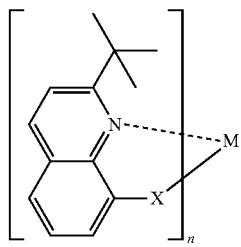

(A-4) 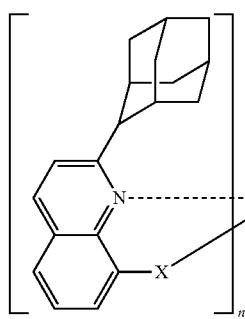

3. A composition comprising one or more compounds of claim 1 and at least one additional functional material selected from the group consisting of fluorescent emitters, phosphorescent emitters, host materials, matrix materials, electron-transport materials, electron-injection materials, hole-conductor materials, hole-injection materials, electron-blocking materials, hole-blocking materials, and n-dopants.

4. The composition of claim 3, wherein the additional functional material is an electron-transport material selected from the group consisting of pyridines, pyrimidines, pyridazines, pyrazines, oxadiazoles, oxazoles, lactams, quinolines, quinoxalines, anthracenes, benzanthracenes, pyrenes, perylenes, benzimidazoles, triazines, ketones, phosphine oxides, and phenazines.

5. The composition of claim 3, wherein the additional functional material is an electron-transport material which comprises a compound of formula (2):

(2) 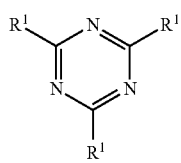

wherein:

$R^1$ is on each occurrence, identically or differently, H, D, F, Cl, Br, I, CHO, $N(R^2)_2$, $N(Ar^1)_2$, $B(Ar^1)_2$, $C(=O)Ar^1$, $P(=O)(Ar^1)_2$, $S(=O)Ar^1$, $S(=O)_2Ar^1$, $CR^2=CR^2Ar^1$, CN, $NO_2$, $Si(R^2)_3$, $B(OR^2)_2$, $B(R^2)_2$, $B(N(R^2)_2)_2$, $OSO_2R^2$, a straight-chain alkyl, alkenyl, alkynyl, alkoxy, or thioalkoxy group having 1 to 40 C atoms or a branched or cyclic alkyl, alkenyl, alkynyl, alkoxy, or thioalkoxy group having 3 to 40 C atoms, each of which is optionally substituted by one or more radicals $R^2$, wherein one or more non-adjacent $CH_2$ groups are optionally replaced by $R^2C=CR^2$, C≡C, $Si(R^2)_2$, $Ge(R^2)_2$, $Sn(R^2)_2$, C=O, C=S, C=Se, $C=NR^2$, $P(=O)(R^2)$, SO, $SO_2$, $NR^2$, O, S, or $CONR^2$ and wherein one or more H atoms are optionally replaced by D, F, Cl, Br, I, CN, or $NO_2$, an aromatic or heteroaromatic ring system having 5 to 60 aromatic ring atoms, which is optionally substituted by one or more radicals $R^2$, or an aryloxy or heteroaryloxy group having 5 to 60 aromatic ring atoms, which is optionally substituted by one or more radicals $R^2$, or a combination of these systems, and wherein two or more adjacent substituents $R^2$ optionally define a mono- or polycyclic, aliphatic or aromatic ring system with one another;

$Ar^1$ is on each occurrence, identically or differently, an aromatic or heteroaromatic ring system having 5 to 30 aromatic ring atoms, which is optionally substituted by one or more radicals $R^2$ and wherein two radicals $Ar^1$ which are bonded to the same nitrogen, phosphorus or boron atom is also optionally linked to one another by a single bond or a bridge selected from the group consisting of $B(R^2)$, $C(R^2)_2$, $Si(R^2)_2$, C=O, C=$NR^2$, C=$C(R^2)_2$, O, S, S=O, $SO_2$, $N(R^2)$, $P(R^2)$, and P(=O)$R^2$;

$R^2$ is on each occurrence, identically or differently, H, D, or an aliphatic, aromatic, and/or heteroaromatic hydrocarbon radical having 1 to 20 C atoms, wherein one or more H atoms are optionally replaced by D or F, and wherein two or more adjacent substituents $R^2$ optionally define a mono- or polycyclic, aliphatic or aromatic ring system with one another.

6. The composition of claim 3, wherein the additional functional material is an n-dopant.

7. A formulation comprising at least one composition of claim 1 and at least one solvent.

8. A formulation comprising at least one composition of claim 3 and at least one solvent.

9. A device comprising at least one composition of claim 1.

10. A device comprising at least one composition of claim 3.

11. The device of claim 9, wherein the device is an electronic device.

12. The device of claim 10, wherein the device is an electronic device.

13. The device of claim 11, wherein the device is an electronic device selected from the group consisting of organic electroluminescent devices, organic integrated circuits, organic field-effect transistors, organic thin-film transistors, organic solar cells, organic optical detectors, organic photoreceptors, and organic field-quench devices.

14. The device of claim 12, wherein the device is an electronic device selected from the group consisting of organic electroluminescent devices, organic integrated circuits, organic field-effect transistors, organic thin-film transistors, organic solar cells, organic optical detectors, organic photoreceptors, and organic field-quench devices.

15. The device of claim 13, wherein it is an organic electroluminescent device selected from the group consisting of organic light-emitting diodes, organic light-emitting transistors, organic light-emitting electrochemical cells, and organic laser diodes.

16. The device of claim 14, wherein it is an organic electroluminescent device selected from the group consisting of organic light-emitting diodes, organic light-emitting transistors, organic light-emitting electrochemical cells, and organic laser diodes.

17. The device of claim 9, wherein the device comprises the at least one composition in an electron-conducting layer.

18. The device of claim 10, wherein the device comprises the at least one composition in an electron-conducting layer.

19. The device of claim 9, wherein the device comprises the at least one composition in an electron-injection layer or in an electron-transport layer.

20. The device of claim 10, wherein the device comprises the at least one composition in an electron-injection layer or in an electron-transport layer.

21. A process for preparing the composition of claim 1 comprising (1) preparing a ligand without metal and (2) reacting the ligand with a metal salt.

* * * * *